United States Patent [19]

Riemer

[11] Patent Number: 5,753,679
[45] Date of Patent: May 19, 1998

[54] BENZYL-PIPERIDINE DERIVATIVES

[75] Inventor: Claus Riemer, Schliengen, Germany

[73] Assignee: Hoffmann-La Roche Inc., Nutley, N.J.

[21] Appl. No.: 634,497

[22] Filed: Apr. 18, 1996

[30] Foreign Application Priority Data

May 10, 1995 [CH] Switzerland .................. 1356/95

[51] Int. Cl.[6] .................................. A01N 43/40
[52] U.S. Cl. .................. 514/327; 514/318; 514/330; 546/194; 546/222; 546/227
[58] Field of Search .................. 546/194, 216, 546/25, 236, 239, 222, 227; 514/318, 327, 330

[56] References Cited

U.S. PATENT DOCUMENTS

| | | | |
|---|---|---|---|
| 4,529,730 | 7/1985 | Schneider et al. | 514/319 |
| 5,169,855 | 12/1992 | Cain et al. | 514/319 |

FOREIGN PATENT DOCUMENTS

| | | |
|---|---|---|
| 0 449 186 | 10/1991 | European Pat. Off. |
| 0 499 187 | 10/1991 | European Pat. Off. |

OTHER PUBLICATIONS

Esenalieva, M.Z. et al, Khim.-Farm. Zh. 1991, 25(4), pp. 22–24.
Bolyard, N. W. et al, J. Am. Chem. Soc. 1929, 51, pp. 924–928.
Kralt, T. et al, Chemical Abstracts, 58:4525d, 1963.
Chemical Abstracts vol. 105, No. 19, Nov. 10, 1986, Abstract No. 172295c, Synthelabo S.A.: "4-benzyloxpiperidine derivatives and their use as antidepressants." pp. 730–731.
Chemical Abstracts vol. 104, No. 15, Apr. 14, 1986, Abstract No. 129918a, R.A. Stokbroekx A: Anti–virally active pyridazinamines, p. 704.
Paul Gilligan, et al, Novel piperidine sigma receptor ligands as potential antipsychotic drugs, Journal of Medicinal Chemistry, vol. 35, No. 23, pp. 4344–4361 (1992).
J. Med. Chem. 1996, 39, 1946–1948.

*Primary Examiner*—C. Warren Ivy
*Assistant Examiner*—Garth M. Dahlen
*Attorney, Agent, or Firm*—George W. Johnston; William H. Epstein; Lewis J. Kreisler

[57] ABSTRACT

Benzly-piperidine derivatives of formula I and their pharmaceutically acceptable salts are used in the control of psychotic disorders which are caused by damage to the dopamine system, especially schizophrenia.

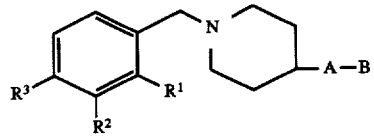

A is

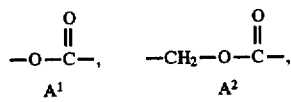

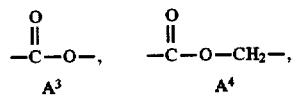

B is

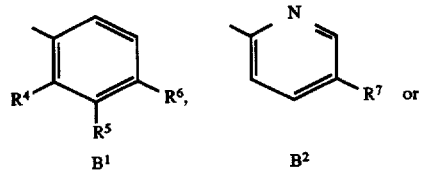

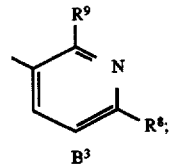

$R^1$, $R^2$ and $R^3$ are independently hydrogen, amino, nitro, halogen, lower-alkly or lower-alkoxy. $R^4$, $R^5$ and $R^6$ are independently hydrogen, nitro, halogen, lower-alkyl, lower-alkoxy, cyano, trifluoromethyl, amino, lower-alkylamino or di-lower-alkylamino. $R^7$, $R^2$ and $R^9$ are independently hydrogen, amino or nitro.

65 Claims, No Drawings

BENZYL-PIPERIDINE DERIVATIVES

SUMMARY OF INVENTION

The invention is concerned with compounds of the general formula

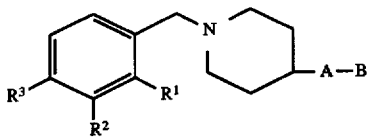

wherein

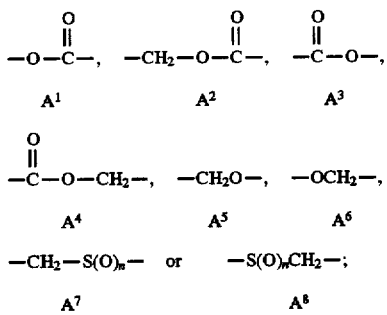

A is n is an integer from 0 to 2;

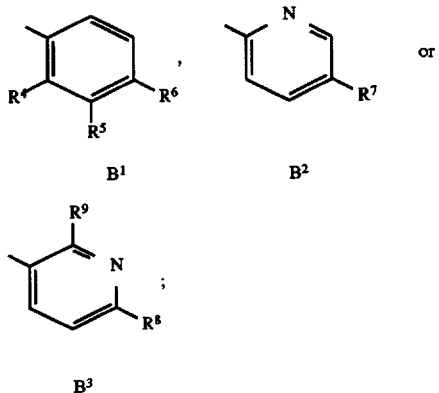

B is $R^1$, $R^2$ and $R^3$ are independently hydrogen, amino, nitro, halogen, lower-alkyl or lower-alkoxy;

$R^4$, $R^5$ and $R^6$ are independently hydrogen, nitro, halogen, lower-alkyl, lower-alkoxy, cyano, trifluoromethyl, amino, lower-alkylamino or di-lower-alkylamino;

$R^7$, $R^8$ and $R^9$ are independently hydrogen, amino or nitro; and pharmaceutically acceptable salts of compounds of formula I.

The compounds of formula I and pharmaceutically acceptable salts thereof useful in control or presentation of psychotic disorders which are caused by damage to the dopamine system, especially schizophrenia.

DETAILED DESCRIPTION

This invention is directed to compounds of the formula

wherein A, B, $R_1$, $R_2$ and $R_a$ are as above and pharmaceutically acceptable salts thereof. The compounds of formula I are useful in the control or prevention of psychotic disorders, especially schizophrenia, which are caused by damage to the dopamine system.

The term "lower-alkyl" used in the present description denotes straight-chain or branched saturated hydrocarbon groups with 1–7 carbon atoms, preferably with 1–4 carbon atoms, such as methyl, ethyl, n-propyl, isopropyl and the like. The term "lower-alkoxy" denotes a lower-alkyl group in the sense of the foregoing definition, which is bonded via an oxygen atom.

The term "halogen" embraces fluorine, chlorine, bromine and iodine.

A methylsulfonyl group can be used, for example, as a "suitable leaving group".

Especially preferred compounds of formula I are those in which A signifies $A^1$ and B signifies $B^1$.

In the compounds of formula I, B can be either $B^1$, $B^2$ or $B^3$. When B is $B^1$, A can be $A^1$, $A^2$, $A^3$, $A^4$, $A^5$, $A^6$, $A^7$ and $A^8$ with $A^1$ being preferred. When A is $A^2$, $A^3$, $A^4$, $A^5$, $A^6$, $A^7$ and $A^8$, B is preferably $B^1$. When A is $A^1$, B can be $B^1$, $B^2$ or $B^3$. When A is $A^2$, $A^3$, $A^4$, $A^5$, $A^6$, $A^7$ and $A^8$ and B is $B^1$, $R^4$, $R^5$ and $R^6$ are preferably hydrogen.

When A is $A^1$ and B is $B^1$, there are included species where $R^1$, $R^2$ and $R^3$ are hydrogen. In this case, $R^4$, $R^5$ and $R^6$ can be hydrogen. On the other hand, one of $R^4$, $R^5$ and $R^6$ can be an amino substituent such as amino, lower alkylamino and dialkylamino with the remainder of said $R^4$, $R^5$ and $R^6$ being hydrogen. Also, in the case where $R^1$, $R^2$ and $R^3$ are hydrogen and one of $R^4$, $R^5$ and $R^6$ is an amino substituent, then at least one of the other of $R^4$, $R^5$ and $R^6$ is a halogen while the remainder of these $R^4$, $R^5$ and $R^6$ substituents being hydrogen. Another embodiment where $R^1$, $R^2$, $R^3$ is hydrogen is where at least one of $R^4$, $R^5$ and $R^6$ is lower alkyl with the remainder of said $R^4$, $R^5$ and $R^6$ being hydrogen. Still another embodiment in this case wherein one of said $R^4$, $R^5$ and $R^6$ is lower alkyl is where the other of said $R^4$, $R^5$ and $R^6$ is halogen, amino, lower-alkoxy or nitro with the remainder of said $R^4$, $R^5$ and $R^6$ being hydrogen. As another embodiment at least one of $R^4$, $R^5$, and $R^6$ can be nitro with the remainder of said $R^4$, $R^5$ and $R^6$ being individually hydrogen, halogen or trifluoromethyl. Still another embodiment is where at least one of said $R^4$, $R^5$, and $R^6$ is lower alkoxy and the remainder of $R^4$, $R^5$ and $R^6$ being hydrogen.

The following are examples of such preferred compounds:

1-(4-Methyl-benzyl)-piperidin-4-yl benzoate,
1-(4-methyl-benzyl)-piperidin-4-yl 4-methyl-benzoate,
1-benzyl-piperidin-4-yl 2-amino-benzoate,
1-benzyl-piperidin-4-yl 4-bromo-benzoate,
1-benzyl-piperidin-4-yl 4-iodo-benzoate,
1-benzyl-piperidin-4-yl 2-methyl-benzoate,
1-benzyl-piperidin-4-yl 4-methyl-benzoate,
1-benzyl-piperidin-4-yl 4-methylamino-benzoate,
1-(4-chloro-benzyl)-piperidin-4-yl benzoate, 1-(4-chloro-benzyl)-piperidin-4-yl 4-methyl-benzoate and 1-(4-chloro-benzyl)-piperidin-4-yl 4-chloro-benzoate.

Compounds in which A is $A^1$ and B is $B^2$ are also particularly preferred, e.g. the compound 1-benzyl-piperidin-4-yl 5-amino-picolinate.

The following are other preferred compounds of general formula I:

1-Benzyl-piperidin-4-yl benzoate,
1-benzyl-piperidin-4-yl 2-fluoro-benzoate,
1-benzyl-piperidin-4-yl 3-fluoro-benzoate,
1-benzyl-piperidin-4-yl 2-chloro-benzoate,
1-benzyl-piperidin-4-yl 2,4-diamino-benzoate,
1-(4-bromobenzyl)-piperidin-4-yl benzoate and
1-(3-nitro-benzyl)-piperidin-4-yl benzoate,
1-benzyl-piperidin-4-yl 2,4-dimethyl-benzoate,
1-(4-fluoro-benzyl)-piperidin-4-yl benzoate,
1-(3-nitro-benzyl)-piperidin-4-yl 4-methyl-benzoate,
1-(3-amino-benzyl)-piperidin-4-yl 4-methyl-benzoate,
1-(2-amino-benzyl)-piperidin-4-yl 4-methyl-benzoate and
1-(4-methoxy-benzyl)-piperidin-4-yl benzoate.

The compounds of formula I and pharmaceutically acceptable salts thereof can be manufactured in accordance with the invention by a) reacting a compound of the formula:

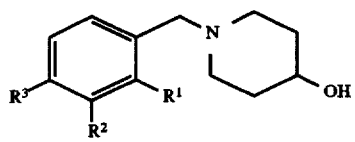

with a compound of the formula

wherein $R^1$–$R^3$ and B have the significance set forth above and R signifies lower-alkoxy, halogen or hydroxy, with the proviso that none of $R^1$–$R^9$ signifies amino and/or alkylamino when R signifies halogen, to give compounds of formula I in which A is $A^1$, b) reacting a compound of the formula:

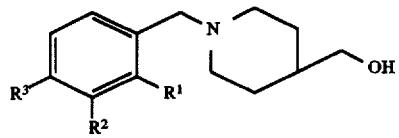

with a compound of formula III, wherein $R^1$–$R^3$, R and B have the significance set forth above, with the proviso as specified under a), to give compounds of formula I in which A is $A^2$, or c) reacting a compound of the formula:

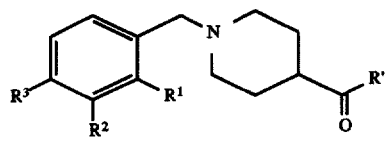

with a compound of the formula

wherein $R^1$–$R^3$ and B have the significance set forth above and R' signifies halogen, with the proviso that none of $R^1$–$R^9$ signifies amino and/or alkylamino, to give compounds of formula I in which A is $A^3$, or d) reacting a compound of general formula V, wherein $R^1$–$R^3$ and R' have the significance set forth above, with a compound of the formula

wherein B is as above, with the proviso that none of $R^4$–$R^9$ signifies amino and/or alkylamino, to give compounds of formula I in which A is $A^4$, or e) reacting a compound of formula IV with a compound of formula VI to give compounds of formula I in which A is $A^5$, or f) reacting a compound of formula 11 with a compound of the formula

wherein R' is as above, with the proviso that none of $R^1$–$R^3$ in formula II is amino, to give compounds of formula I in which A is $A^6$, or g) reacting a compound of the formula

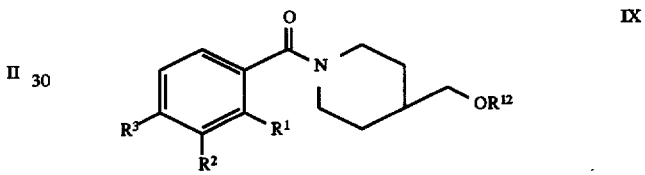

with a compound of the formula:

wherein $R^1$–$R^3$ and B are as above and $R^{12}$ is a suitable leaving group, and subsequently reducing to give compounds of formula I in which A is $A^7$, or h) reacting a compound of the formula

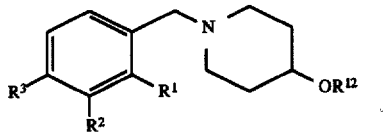

with a compound of the formula

wherein $R^1$–$R^3$, $R^{12}$ and B are as above, with the proviso that none of $R^1$–$R^3$ is amino, to give compounds of formula I in which A is $A^8$, or i) reducing sulfanyl groups in compounds of formula I in which A is $A^7$ or $A^8$ to sulfinyl groups and/or sulfonyl groups, or j) reducing nitro groups of compounds of formula I to amino groups, or k) cleaving off protecting group(s), or l) alkylating amino groups to lower-alkylamino or di-lower-alkylamino groups, and m) converting a compound of general formula I into a pharmaceutically usable salt.

In accordance with process embodiment a) an appropriately substituted benzyl-4-hydroxypiperidine compound (II)

is reacted with suitable alkyl benzoates, benzoyl halides, benzoic acids, alkyl picolinates, picolinyl halides, picolinic acids, alkyl nicotinates, nicotinoyl halides or nicotinic acids (III).

The following are especially well suited as compounds of formula II: 1-Benzyl-4-hydroxypiperidine, 1-(2-bromo-benzyl)-piperidin-4-ol, 1-(3-bromo-benzyl)-piperidin-4-ol, 1-(4-bromo-benzyl)-piperidin-4-ol, 1-(2-chloro-benzyl)-piperidin-4-ol, 1-(3-chloro-benzyl)-piperidin-4-ol, 1-(4-chloro-benzyl)-piperidin-4-ol, 1-(2-fluoro-benzyl)-piperidin-4-ol, 1-(3-fluoro-benzyl)-piperidin-4-ol, 1-(4-fluoro-benzyl)-piperidin-4-ol, 1-(2-nitro-benzyl)-piperidin-4-ol, 1-(2-amino-benzyl)-piperidin-4-ol, 1-(3-nitro-benzyl)-piperidin-4-ol, 1-(4-nitro-benzyl)-piperidin-4-ol, 1-(4-methyl-benzyl)-piperidin-4-ol, 1-(4-methoxy-benzyl)-piperin-4-ol and the like.

Suitable reaction partners of formula III for compounds of formula 11 in accordance with process embodiment a) are preferably the following: 4-amino-benzoate, 3-nitro-benzoyl chloride, 2-nitro-benzoyl chloride, 4-nitro-benzoyl chloride, benzoyl chloride, 5-nitro-picolinic acid, 6-trifluoroacetamido-nicotinic acid, 2-amino-nicotinic acid, 2-fluorobenzoyl chloride, 3-fluoro-benzoyl chloride, 4-fluoro-benzoyl chloride, 3-chloro-benzoyl chloride, 4-chloro-benzoyl chloride and the like.

The reaction in accordance with this process embodiment is effected according to methods known per se. Conveniently, where R in formula III signifies lower-alkoxy a compound of general formula II is dissolved in toluene, deprotonized with, for example, sodium hydride under a protective gas atmosphere and then reacted with a compound of formula III.

A further possibility comprises dissolving a compound of formula II in DMF and reacting in the presence of 4-dimethyl-aminopyridine and a compound of formula III with N-ethyl-N'-(3-dimethylaminopropyl)-carbodiimide.

When R in formula III is halogen, a compound of formula III is conveniently dissolved in toluene under a protective gas atmosphere and this solution is subsequently treated with a compound of formula II in the presence of triethylamine. When the compound of formula III has a free acid group, this is conveniently treated with carbonyidiimidazole in THF, stirred while heating and subsequently reacted with a compound of formula II.

In accordance with process embodiment b) the 1-benzyl-4-hydroxymethyl-piperidine compound or derivative thereof (IV), which can have the same substituents as the described compounds of formula II, is reacted with a compound of formula III. This reaction is conveniently effected under similar conditions to those described under a). The type of reaction also depends here on the significance of R in formula III.

In accordance with embodiment c) a compound of formula V, for example 1-benzyl-piperidine-4-carbonyl chloride, 1-(2-bromobenzyl)-piperidine-4-carbonyl chloride and the like, is reacted with phenol or an appropriately substituted derivative thereof or with a suitable picoline or nicotine hydroxide to give compounds of general formula I. This is conveniently carried out by dissolving a compound of formula V in toluene, treating with triethylamine and then reacting with a compound of general formula VI.

Compounds of formula I in which A is $A^4$ are obtained according to process embodiment d). Compounds of formula V, which have been described above, are conveniently used and these compounds are reacted with benzyl alcohol or with an appropriately substituted derivative thereof or with a picoline-or nicotinemethyl alcohol. The reaction is effected by boiling under reflux conditions in toluene.

In accordance with process embodiment e) a compound of formula IV, for example 1-benzyl-4-hydroxymethyl-piperidine or derivative thereof, is reacted with a compound of formula VI, for example with phenol, an appropriately substituted derivative thereof or with a suitable picoline or nicotine hydroxide. Conveniently, the corresponding compounds of formula IV and VI are dissolved in a solvent, for example toluene, in the presence of triphenylphosphine, cooled to about 10° C., treated with diethyl azodicarboxylate and stirred while heating for several hours.

According to process embodiment f) compounds of formula II which have been described above, are reacted with benzyl halides, with their derivatives, or with corresponding picoline- or nicotinemethyl halides of formula VIII. This is conveniently carried out as follows: A compound of formula II is added dropwise at about 0° C. to a suspension of sodium hydride and dimethylformamide. After reaching room temperature the mixture is treated with a corresponding compound of formula VIII, for example with benzyl bromide.

Compounds of formula I in which A is $A^7$ or $A^8$ are obtained according to embodiments g) and h).

Process embodiment g) is conveniently carried out as follows: sodium hydride suspended in THF is treated with a compound of formula X, for example with thiophenol or with its derivatives, and boiled at reflux for several hours after the addition of a compound of formula IX, for example 1-benzoyl-piperidin-4-ylmethyl methanesulfonate. The desired compounds of formula I are obtained after reduction with borohydride in THF.

The reaction in accordance with process embodiment h) is effected analogously to that described under g). Sodium hydride is suspended in THF and treated with a compound of formula XII, for example with benzyl mercaptan or with its derivatives.

Subsequently, after the addition of a compound of formula XI, for example 1-benzyl-piperidin-4-yl methanesulfonate, the mixture is boiled at reflux for several hours.

The compounds of formula I described in embodiments g) and h) have sulfanyl groups which can be oxidized in accordance with variant i) to sulfinyl groups and/or sulfonyl groups. This is conveniently effected according to methods known per se, for example with sodium periodate.

According to process embodiment j) nitro groups present in the compounds of formula I can be reduced to amino groups according to methods known per se. The reduction is preferably effected with Raney-nickel at room temperature under normal pressure.

Process embodiment k) comprises the cleavage of protecting groups, for example of amino protecting groups. This method is also known in the literature. Conveniently, a compound which contains an amino protecting group is suspended in aqueous piperidine in an ultrasound bath and subsequently stirred for several hours, with a corresponding compound of general formula I being obtained after working-up.

An amino group present in a compound of formula I is alkylated to a lower-alkylamino group or to a di-lower-alkylamino group according to process embodiment 1). This can be conveniently carried out as follows: a compound of formula I which contains an amino group is dissolved in acetonitrile and treated with e.g. formaldehyde and $NaBH_3CN$. After adjusting to pH 6 using, for example, glacial acetic acid this procedure is repeated, with a methylamino compound of formula I being obtained after a reaction period of about 2 hours. Another method comprises treating a compound of formula I which contains an amino group with, for example, formic acid and subsequently hydrogenating in a $BH_3$—THF solution.

The salt formation in accordance with embodiment m) of the process in accordance with the invention is effected according to methods which are generally usual and which will be familiar to any person skilled in the art. The basic compounds of formula I can be converted into pharmaceutically acceptable acid addition salts, for example with hydrogen chloride, hydrogen bromide, phosphoric acid, sulfuric acid, citric acid, p-toluenesulfonic acid and the like.

The starting materials of formulae III, VI, VII, VII, X and XII are known compounds or can be prepared from known compounds according to generally usual methods. The preparation of the intermediates II, IVa, V, IX and XI can be effected in accordance with Schemes 1, 2 or 3 and is described in detail in the Examples.

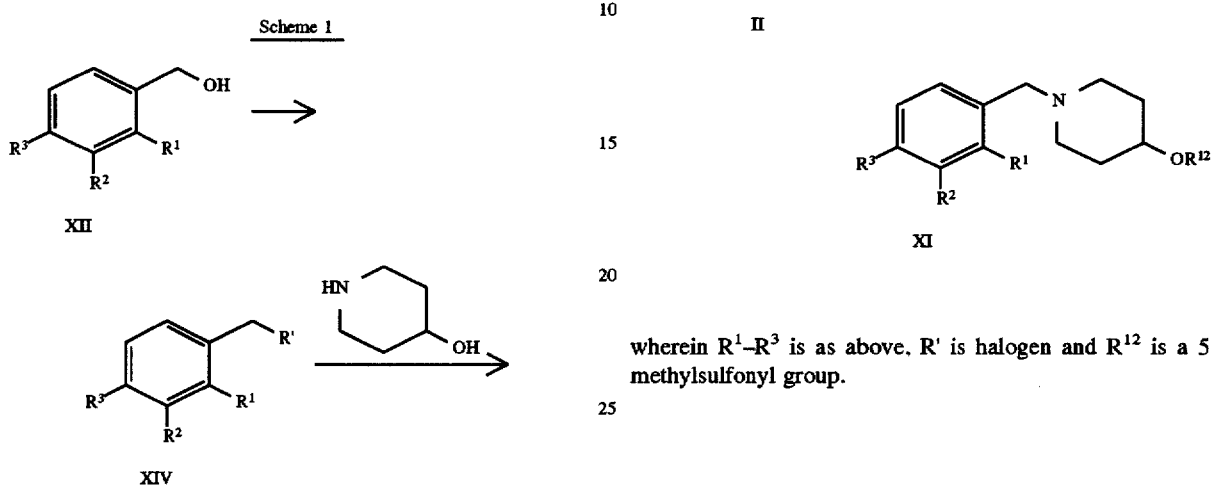

Scheme 1 wherein $R^1$–$R^3$ is as above, R' is halogen and $R^{12}$ is a methylsulfonyl group.

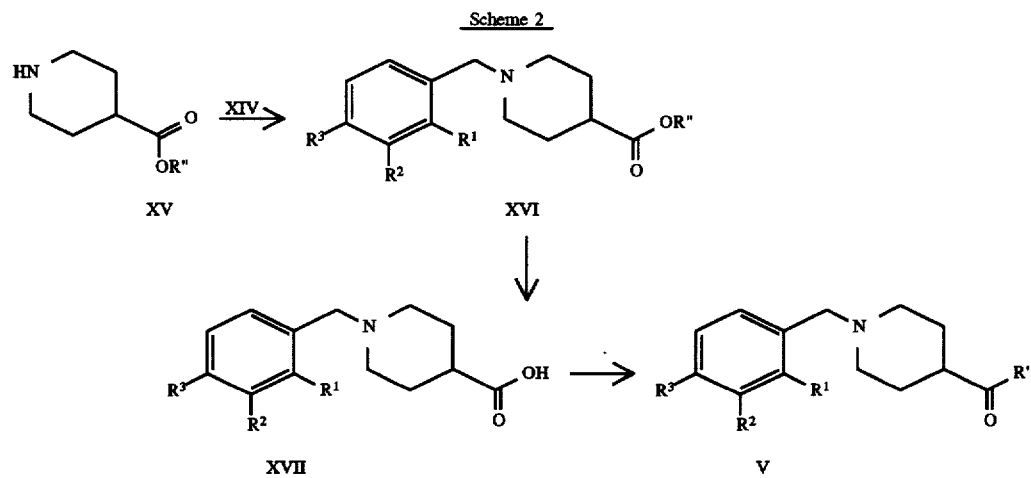

Scheme 2 wherein $R^1$–$R^3$ and R' are as above and R" is lower-alkyl.

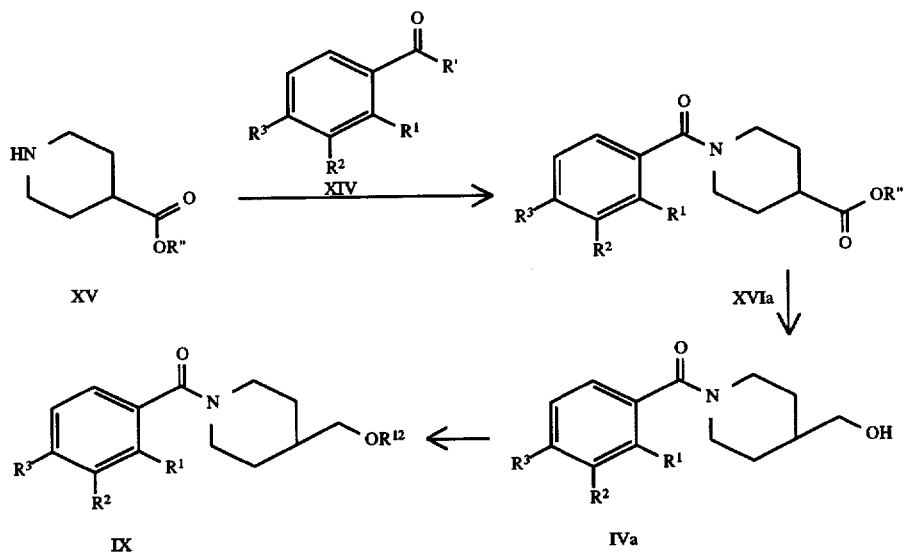

wherein $R^1$-$R^3$, R', R" and $R^{12}$ are as above.

As mentioned earlier, the compounds of formula I in accordance with the invention have valuable pharmacological properties. They have a high selective affinity to a neuroreceptor, in particular to the dopamine $D_4$ receptor, and can accordingly be used for the treatment or prevention of psychotic disorders such as schizophrenia. By virtue of the high selectivity of these compounds to the dopamine $D_4$ neuroreceptor it can be expected that significantly less side effects will occur with the use of these compounds than with known classical neuroleptic agents, e.g. haloperidol, which, as is known, bind to the $D_2$ or $D_3$ receptor. It has been established that in the case of schizophrenia the $D_2$ and $D_3$ receptor density increases by about 10%, while it increases by about 600% in the case of the $D_4$ receptor (TiPS, July 1994, vol. 15, p. 264–70).

Test Description

The compounds were characterized by a comparison in binding behaviour to the D4 receptor and to the $D_2$ receptor. CHO cells (Chinese Hamster Ovary) were used in the test. Crude membranes were isolated from $D_4$—CHO and $D_2$—CHO cells by ultracentrifugation and were stored at −80° C. After thawing and homogenization in a buffer solution (50 mM Tris, 1 mM EDTA, 5 mM KCl, 1.5 mM CaCl2, 4 mM $MgCl_2$, pH 7.4) they were incubated at room temperature for 90 minutes with 200 pM [$^3$H]-spiperone and increasing concentrations ($1\times10^{-11}$M to $1\times10^{-4}$M) of the test compound. A non-specific binding by the incubation was established in the presence of $1\times10^{-5}$M (+)-butaclamol.

The unbound radioligand was removed by filtration through a GF/C glass filter and the bound radioactivity was determined by flash emission in a Packard Top Count.

The following Table shows a comparison in the binding behaviour of the compounds in accordance with the invention to the $D_4$ receptor and D2 receptor.

The Ki value is a binding constant which shows the affinity of the compounds for the $D_4$ receptor. It was determined using $^3$H-spiperone. The calculation of the value was effected with a ligand.

The 2nd column with activity data clearly shows the selectivity with respect to the $D_2$ receptor, expressed by the ratio of the Ki values at the $D_4$ receptor and at the $D_2$ receptor.

| Compound/Example | Ki at $D_4$ [uM] | Sel. vs. $D_2$ |
|---|---|---|
| A/5a | 4 | 971 |
| B/8b | 16.4 | 903 |
| C/19b | 10 | 800 |
| D/22a | 15 | 750 |
| E/24a | 6 | 476 |
| F/25a | 8 | 940 |
| G/32b | 5 | 814 |
| H/58c | 7.3 | 663 |
| I/59a | 15 | 619 |
| J/82a | 18 | 519 |
| k/78b | 3.8 | 1690 |
| L/79a | 5.2 | 1556 |
| M/70b | 13 | 764 |
| N/46a | 9 | 332 |
| O/64b | 18 | 533 |
| P/71a | 19 | 602 |
| Q/73a | 19 | 549 |
| R/69a | 17.5 | 600 |
| S/80c | 15 | 703 |

A 1-Benzyl-piperidin-4-yl 2-amino-benzoate
B 1-benzyl-piperidin-4-yl 5-amino-picolinate
C 1-benzyl-piperidin-4-yl 4-bromo-benzoate
D 1-benzyl-piperidin-4-yl 4-iodo-benzoate
E 1-benzyl-piperidin-4-yl 2-methyl-benzoate
F 1-benzyl-piperidin-4-yl 4-methyl-benzoate
G 1-benzyl-piperidin-4-yl 4-methylamino-benzoate
H 1-(4-chloro-benzyl)-piperidin-4-yl benzoate
I 1-(4-chloro-benzyl)-piperidin-4-yl 4-methyl-benzoate
J 1-(4-chloro-benzyl)-piperidin-4-yl 4-chloro-benzoate
K 1-(4-methyl-benzyl)-piperidin-4-yl benzoate
L 1-(4-methyl-benzyl)piperidin-4-yl 4-methyl-benzoate
M 1-(3-Nitro-benzyl)-piperidin-4-yl benzoate
N 1-Benzyl-piperidin-4-yl 2,4-dimethyl-benzoate
O (4-Fluoro-benzyl)-piperidin-4-yl benzoate
P 1-(3-Nitro-benzyl)-piperidin-4-yl 4-methyl-benzoate
Q 1-(3-Amino-benzyl)-piperidin-4-yl 4-methyl-benzoate
R 1-(2-Amino-benzyl)-piperidin-4-yl 4-methyl-benzoate
S 1-(4-Methoxy-benzyl)-piperidin-4-yl benzoate.

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Adjuvants such as alcohols, polyols, glycerol, vegetable oils and the like can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical administration form together with one or more therapeutically inert carriers. The dosage can vary within wide limits and will, of course, be fitted to the individual requirements in each particular case. In general, in the case of intravenous administration a daily dosage of about 1 mg to 1000 mg should be appropriate.

Finally, as mentioned earlier, the use of compounds of formula I and of pharmaceutically usable salts thereof for the production of medicaments, especially for the control or prevention of psychotic disorders, for example schizophrenia, Parkinson's disease and Huntington's chorea, is also an object of the invention.

The following Examples are intended to illustrate the present invention in more detail, but do not limit its scope in any manner.

EXAMPLE 1

1-Benzyl-piperidin-4-yl 4-amino-benzoate 3.98 g (0.02 mol) of 1-benzyl-4-hydroxy-piperidine in 70 ml of toluene were treated with 0.624 g of NaH (50%) and heated at reflux for 1 ½ hr. while gassing with argon. Subsequently, 3.32 g (0.022 mol) of methyl 4-amino-benzoate dissolved in 80 ml of toluene were added dropwise over ½ hr. and the mixture was heated at reflux for a further 2 hrs. The suspension obtained was added to 400 ml of water and the mixture was stirred. The precipitate was filtered off under suction and washed with toluene and hexane. The organic phase of the filtrate was separated, washed three times with water, dried over $MgSO_4$ and evaporated and the residue was combined with the filter material. Chromatography was carried out over silica gel with chloroform as the eluent and recrystallization was carried out from ethyl acetate/hexane. 2.4 g (38.7%) of 1-benzyl-piperidin-4-yl 4-amino-benzoate were obtained as colorless crystals; m.p. 119°–120° C.

EXAMPLE 2

1-Benzyl-piperidin-4-yl 3-nitro-benzoate a) 0.388 g (0.0021 mol) of 3-nitro-benzoyl chloride were dissolved in 20 ml of toluene under argon and treated while stirring with 0.5 g (0.0026 mol) of 1-benzyl-4-hydroxy-piperidine and 0.643 ml (0.0046 mol) of triethylamine. After boiling at reflux for 2 hrs. the suspension was filtered and the filtrate was completely freed from solvent. The residue was chromatographed over silica gel with ethyl acetate/hexane 1:2 as the eluent. 0.65 g (92%) of 1-benzyl-piperidin-4-yl 3-nitro-benzoate was obtained as a yellow oil. MS: mele (% basic peak)=340 ($C_{19}H_{20}N_2O_4^+$, 27), 263 (25), 173 (36.5), 150 (14.5), 91 (100), 82 (100).

b) 0.1 g (0.0029 mol) of 1-benzyl-piperidin-4-yl 3-nitro-benzoate was dissolved in 5 ml of ether and treated with 3 ml of 1N ethereal HCl. The precipitate was filtered off, washed with ether and recrystallized from ethanol/ether. 0.095 g (87%) of 1-benzyl-piperidin-4-yl 3-nitro-benzoate hydralkylaminoochloride (1:1) was obtained as white crystals; m.p. 230°.

EXAMPLE 3

1-Benzyl-piperidin-4-yl 3-amino-benzoate a) 0.5 g (0.00147 mol) of 1-benzyl-piperidin-4-yl 3-nitro-benzoate was dissolved in 20 ml of ethanol and treated with 0.3 g of Raney-nickel under argon. The mixture was hydrogenated at room temperature under normal pressure for 4 hrs. The catalyst was filtered off, the filtrate was concentrated and the residue was chromatographed over silica gel with ethyl acetate/hexane 1:1 as the eluent. 0.372 g (82%) of 1-benzyl-piperidin-4-yl 3-amino-benzoate was obtained as white crystals; m.p. 70°–71°.

b) 0.1 g (0.00032 mol) of 1-benzyl-piperidin-4-yl 3-amino-benzoate was dissolved in 5 ml of ether and treated with 3 ml of 1N ethereal HCl. The precipitate was filtered off, washed with ether and recrystallized from ether/ethanol. 0.08 g (65%) of 1-benzyl-piperidin-4-yl 3-amino-benzoate hydrochloride (1:1) was obtained as white crystals; m.p. 180° (dec.).

EXAMPLE 4

1-Benzyl-piperidin-4-yl 2-nitro-benzoate a) 1.55 g (0.00837 mol) of 2-nitro-benzoyl chloride were dissolved in 70 ml of toluene and treated with 2.0 g (0.0104 mol) of 1-benzyl-4-hydroxypiperidine and 2.6 ml (0.0184 mol) of triethylamine. After boiling under reflux for 18 hrs. the suspension was filtered, the filtrate was concentrated and the residue was chromatographed over silica gel with ethyl acetate/hexane (1:2–>1:1) as the eluent. 1.7 g (60%) of 1-benzyl-piperidin-4-yl 2-nitro-benzoate were obtained as yellow crystals; m.p. 98°–99°.

b) 0.15 g (0.00044 mol) of 1-benzyl-piperidin-4-yl 2-nitro-benzoate were dissolved in 7 ml of ether and treated with 5 ml of 1N ethereal HCl. The precipitate was filtered off under suction, washed with ether and recrystallized from ethanol/ether. 0.096 g (58%) of 1-benzyl-piperidin-4-yl 2-nitro-benzoate hydrochloride (1:1) was obtained as white crystals; m.p. 160°–161°.

EXAMPLE 5

1-Benzyl-piperidin-4-yl 2-amino-benzoate a) 0.5 g (0.00147 mol) of 1-benzyl-piperidin-4-yl 2-nitro-benzoate was dissolved in 20 ml of ethanol and treated with 0.05 g of Raney-nickel. The mixture was hydrogenated at room temperature under normal pressure for 24 hrs. The catalyst was filtered off and the solvent was removed completely. The residue was chromatographed over silica gel with ethyl acetate/hexane (1:1) as the eluent. 0.322 g (71%) of 1-benzyl-piperidin-4-yl 2-amino-benzoate was obtained as yellow crystals; m.p. 87°–88°.

b) 0.1 g (0.00032 mol) of 1-benzyl-piperidin-4-yl 2-amino-benzoate was dissolved in 5 ml of ether and treated with 3 ml of 1N ethereal HCl. The precipitate was filtered off under suction, washed with ether and recrystallized from ethanol/ether. 0.08 g (65%) of 1-benzyl-piperidin-4-yl 2-amino-benzoate hydrochloride (1:1.95) was obtained as white crystals; m.p. >193 (dec.).

EXAMPLE 6

1-Benzyl-piperidin-4-yl 4-nitro-benzoate a) 0.5 g (0.00216 mol) of 1-benzyl-4-hydroxypiperidine and 0.64 ml (0.0046 mol) of triethylamine were dissolved in 20 ml of toluene, treated with 0.5 g (0.0027 mol) of 4-nitro-benzoyl chloride and boiled at reflux for 6 hrs. The suspension was filtered, the filtrate was concentrated and the residue was chromatographed over silica gel with ethyl acetate/hexane (1:3) as the eluent. 0.78 g (85%) of 1-benzyl-piperidin-4-yl 4-nitro-benzoate was obtained as yellow crystals; m.p. 87°–89°.

b) 0.255 g (0.00075 mol) of 1-benzyl-piperidin-4-yl 4-nitro-benzoate was dissolved in 22.5 ml of ether and 1 ml of methanol, treated with 7.5 ml of 1N ethereal HCl and stirred for 1 hr. The precipitate was filtered off under suction, washed with ether and dried. 0.265 g (94%) of 1-benzyl-piperidin-4-yl 4-nitro-benzoate hydrochloride (1:1) was obtained as white crystals; m.p. 243°–245°.

EXAMPLE 7

1-Benzyl-piperidin-4-yl benzoate a) 0.5 g (0.00216 mol) of 1-benzyl-4-hydroxypiperidine and 0.64 ml (0.0046 mol) of triethylamine were dissolved in 20 ml of toluene, treated with 0.313 ml (0.0027 mol) of benzoyl chloride and boiled at reflux for 6 hrs. The suspension was filtered, the filtrate was concentrated and the residue was chromatographed over silica gel with ethyl acetate/hexane (1:3) as the eluent. 0.525 g (82%) of 1-benzyl-piperidin-4-yl benzoate was obtained as yellowish oil.

b) 0.221 g (0.00075 mol) of 1-benzyl-piperidin-4-yl benzoate was dissolved in 22.5 ml of ether, filtered and treated with 1 ml of methanol and 7.5 ml of 1N ethereal HCl. After stirring for 1 hr. the precipitate was filtered off, washed with ether and dried. 0.23 g (92%) of 1-benzyl-piperidin-4-yl benzoate hydrochloride (1:1) was obtained as white crystals; m.p. 231°–233°.

EXAMPLE 8

1-Benzyl-piperidin-4-yl 5-nitro-picolinate a) 5.0 g (0.03 mol) of 5-nitro-picolinic acid (Pharmazie 38 (1983), p. 593) and 4.87 g (0.03 mol) of carbonyldiimidazole were dissolved in 250 ml of THF and stirred at 60° for 3 hours. The mixture was subsequently treated with 5.75 g (0.03 mol) of 1-benzyl-4-hydroxy-piperidine, stirred at 0°–5° for 18 hrs., at room temperature for 3 hrs. and subsequently at 40° for 2 hrs. The reaction mixture was completely freed from solvent and the residue was chromatographed over neutral Alox (grade II) with dichloromethane as the eluent and recrystallized from ethyl acetate. 4.2 g (41%) of 1-benzyl-piperidin-4-yl 5-nitro-picolinate were obtained as yellow crystals; m.p. 175°–176°.

b) 3.0 g (0.0088 mol) of 1-benzyl-piperidin-4-yl 5-nitro-picolinate were dissolved in 500 ml of THF, treated with 1.0 g of Raney-nickel and hydrogenated for 51 hrs. The catalyst was filtered off, the filtrate was concentrated to a volume of 100 ml and 8.4 ml of ethyl acetate HCl (17.9% wt./vol.) were added. The resulting precipitate was filtered off under suction, washed with ether and dried. 2.8 g (84%) of 1-benzyl-piperidin-4-yl 5-nitro-picolinate hydrochloride (5:9) were obtained as yellowish crystals.

EXAMPLE 9

1-Benzyl-piperidin-4-yl 6-amino-nicotinate a) 0.53 ml (0.0038 mol) of trifluoroacetic anhydride was added at 0° to a suspension of 0.5 g (0.0036 mol) of 6-amino-nicotinic acid in 70 ml of THF. The mixture was stirred at room temperature for 2 hrs., whereby almost all passed into solution, a further 0.2 ml (0.0014 mol) of trifluoroacetic anhydride was added and the mixture was subsequently heated to 50° for 1 hr. The solvent was removed completely and the white residue was suspended in 35 ml of water and treated in an ultra-sound bath for ½ hr. Thereafter, the mixture was suction filtered and the filter material was washed with water and dried. 0.442 g (53%) of 6-trifluoroacetamido-nicotinic acid was obtained as white crystals; m.p. >255°.

b) 0.1 g (0.00043 mol) of 6-trifluoroacetamido-nicotinic acid was dissolved in 10 ml of THF, treated with 0.073 g (0.00045 mol) of carbonyldiimidazole and stirred at 60° for 2 hrs. Then, 0.086 g (0.00045 mol) of 1-benzyl-4-hydroxypiperidine was added and the mixture was stirred at 60° overnight. The reaction mixture was concentrated and the residue was chromatographed over silica gel with ethyl acetate/hexane (1:1) as the eluent. 0.097 g (72%) of 1-benzyl-piperidin-4-yl 6-amino-nicotinate was obtained as white crystals; m.p. 135°–136°.

c) 0.06 g (0.00015 mol) of 1-benzyl-piperidin-4-yl 6-amino-nicotinate was dissolved in 40 ml of ether, treated with 2 ml of 1N ethereal HCl and treated in an ultrasound bath for 1 hr. The precipitate was filtered off under argon, washed with ether and dried in a high vacuum (0.3 Torr). 0.053 g (92%) of 1-benzyl-piperidin-4-yl 6-amino-nicotinate hydrochloride (1:1.95) was obtained as a beige, amorphous and hygroscopic solid. MS: me/e=312 ($C_{18}H_{21}N_3O_2+$).

EXAMPLE 10

1-Benzyl-piperidin-4-yl 2-amino-nicotinate a) 0.14 g (0.00101 mol) of 2-amino-nicotinic acid was suspended in 50 ml of THF and treated with 0.077 ml (0.00101 mol) of trifluoroacetic acid. The mixture was stirred at room temperature for 1 hr., whereby a solution resulted. To this was added 0.25 g (0.0015 mol) of carbonyldiimidazole and the mixture was stirred at room temperature for 2 hrs. Subsequently, 0.34 g (0.00178 mol) of 1-benyl-4-hydroxy-piperidine was added and the mixture was stirred at 60° for 72 hrs. After removing the solvent the residue was chromato-graphed over silica gel with ethyl acetate/hexane (1:1) as the eluent. 0.105 g (31%) of 1-benzyl-piperidin-4-yl 2-amino-nicotinate was obtained as white crystals. MS: me/e (% basic peak)=311 ($C_{18}H_{21}N_3O_2^+$, 7.5), 173 (42), 91 (100), 82 (86).

b) 0.1 g (0.00032 mol) of 1-benzyl-piperidin-4-yl 2-amino-nicotinate was dissolved in 10 ml of ether and 0.3 ml of methanol, filtered and treated with 3.2 ml of 1N ethereal HCl. After completely removing the solvent the residue was treated several times with ether and again concentrated. 0.105 g (86%) of 1-benzyl-piperidin-4-yl 2-amino-nicotinate hydrochloride (1:1.9) was obtained as yellowish crystals; m.p. 230° (dec.).

EXAMPLE 11

1-Benzyl-piperidin-4-yl 2-fluoro-benzoate a) 0.5 g (0.0026 mol) of 1-benzyl-4-hydroxypiperidine and 0.64 ml (0.0046.mol). of triethylamine were dissolved in 20 ml of toluene and treated with 0.32 ml (0.0027 mol) of 2-fluoro-benzoyl chloride. The mixture was boiled at reflux for 6 hrs., the precipitate was filtered off and the filtrate was concentrated. The residue was chromatographed over silica gel with ethyl acetate/hexane (1:1). 0.68 g (83%) of 1-benzyl-piperidin-4-yl 2-fluoro-benzoate was obtained as a colorless oil.

b) 0.235 g (0.00075 mol) of 1-benzyl-piperidin-4-yl 2-fluoro-benzoate was dissolved in 22.5 ml of ether and 1 ml of methanol and treated with 7.5 ml of 1N ethereal HCl. The mixture was stirred for 2 hrs. and the resulting precipitate was filtered off, washed with ether and dried. 0.21 g (79%) of 1-benzyl-piperidin-4-yl 2-fluoro-benzoate hydrochloride (1:1) was obtained as white crystals; m.p. 188°–190°.

EXAMPLE 12

1-Benzyl-piperidin-4-yl 3-fluoro-benzoate a) 0.5 g (0.0026 mol) of 1-benzyl-4-hydroxypiperidine and 0.64 ml (0.0046 mol) of triethylamine were dissolved in 20 ml of toluene and treated with 0.32 ml (0.0027 mol) of 3-fluoro-benzoyl chloride. The mixture was boiled at reflux for 6 hrs., the precipitate was filtered off and the filtrate was concentrated. The residue was chromatographed over silica gel with ethyl acetate/hexane (1:1). 0.72 g (88%) of 1-benzyl-piperidin-4-yl 3-fluoro-benzoate was obtained as a colorless oil.

b) 0.235 g (0.00075 mol) of 1-benzyl-piperidin-4-yl 3-fluoro-benzoate was dissolved in 22.5 ml of ether and 1 ml of methanol and treated with 7.5 ml of 1N ethereal HCl. The mixture was stirred for 2 hrs. and the resulting precipitate was filtered off, washed with ether and dried. 0.21 g (79%) of 1-benzyl-piperidin-4-yl 3-fluoro-benzoate hydrochloride (1:1) was obtained as white crystals; m.p. 228°–230°.

EXAMPLE 13

1-Benzyl-piperidin-4-yl 3-fluoro-benzoate a) 0.5 g (0.0026 mol) of 1-benzyl-4-hydroxypiperidine and 0.64 ml (0.0046 mol) of triethylamine were dissolved in 20 ml of toluene and treated with 0.32 ml (0.0027 mol) of 4-fluoro-benzoyl chloride. The mixture was boiled at reflux for 6 hrs., the precipitate was filtered off and the filtrate was concentrated. The residue was chromatographed over silica gel with ethyl acetate/hexane (3:1). 0.59 g (87%) of 1-benzyl-piperidin-4-yl 4-fluoro-benzoate was obtained as a greenish oil.

b) 0.235 g (0.00075 mol) of 1-benzyl-piperidin-4-yl 4-fluoro-benzoate was dissolved in 22.5 ml of ether and 1 ml of methanol and treated with 7.5 ml of 1N ethereal HCl. The mixture was stirred for 2 hrs. and the resulting precipitate was filtered off, washed with ether and dried. 0.23 g (88%) of 1-benzyl-piperidin-4-yl 4-fluoro-benzoate hydrochloride (1:1) 25 was obtained as white crystals; m.p. 220°–222°.

EXAMPLE 14

1-Benzyl-piperidin-4-yl 2-chloro-benzoate a) 0.2 g (0.00105 mol) of 1-benzyl-4-hydroxypiperidine and 0.26 ml (0.00184 mol) of triethylamine were dissolved in 10 ml of toluene and treated with 0.11 ml (0.00084 mol) of 2-chloro-benzoyl chloride. The mixture was boiled at reflux for 6 hrs., the precipitate was filtered off and the filtrate was concentrated. The residue was chromatographed over silica gel with ethyl acetate/hexane (1:2). 0.262 g (95%) of 1-benzyl-piperidin-4-yl 2-chloro-benzoate was obtained as white crystals; m.p. 143°–144°.

b) 0.1 g (0.0003 mol) of 1-benzyl-piperidin-4-yl 2-chloro-benzoate was dissolved in 5 ml of ether and 0.5 ml of methanol and treated with 1 ml of 1N ethereal HCl. The mixture was stirred for 2 hrs. and the resulting precipitate was filtered off, washed with ether and dried. 0.095 g (86%) of 1-benzyl-piperidin-4-yl 2-chloro-benzoate hydrochloride (1:1) was obtained as white crystals; m.p. 200°–202°.

EXAMPLE 15

1-Benzyl-piperidin-4-yl 3-chloro-benzoate a) 0.5 g (0.0026 mol) of 1-benzyl-4-hydroxypiperidine and 0.64 ml (0.0046 mol) of triethylamine were dissolved in 20 ml of toluene and treated with 0.27 ml (0.0021 mol) of 3-chloro-benzoyl chloride. The mixture was boiled at reflux for 6 hrs., the precipitate was filtered off and the filtrate was concentrated. The residue was chromatographed over silica gel with ethyl acetate/hexane (1:2). 0.566 g (82%) of 1-benzyl-piperidin-4-yl 3-chloro-benzoate was obtained as a yellow oil. MS: mele (% basic peak)=329 ($C_{19}H_{20}ClNO_2^+$, 10), 252 (10), 173 (35), 139 (15), 91 (100), 82 (100).

b) 0.1 g (0.0003 mol) of 1-benzyl-piperidin-4-yl 3-chloro-benzoate was dissolved in 5 ml of ether and 0.5 ml of methanol and treated with 1 ml of 1N ethereal HCl. The mixture was stirred for 2 hrs. and the resulting precipitate was filtered off, washed with ether and dried. 0.095 g (86%) of 1-benzyl-piperidin-4-yl 3-chloro-benzoate hydrochloride (1:1) was obtained as white crystals, m.p. 212°–213°.

EXAMPLE 16

1-Benzyl-piperidin-4-yl 4-chloro-benzoate a) 0.3 g (0.0015 mol) of 1-benzyl-4-hydroxypiperidine and 0.216 ml (0.00155 mol) of triethylamine were dissolved in 20 ml of toluene and treated with 0.21 ml (0.0016 mol) of 4-chloro-benzoyl chloride. The mixture was boiled at reflux for 6 hrs., the precipitate was filtered off and the filtrate was concentrated. The residue was chromatographed over silica gel with ethyl acetate/hexane (1:2). 0.404 g (82%) of 1-benzyl-piperidin-4-yl 4-chloro-benzoate was obtained as a colorless oil. MS: me/e (% basic peak)=329 ($C_{19}H_{20}ClNO_2^+$, 7), 252 (7), 173 (32), 139 (15), 91 (91), 82 (100).

b) 0.363 g (0.001 mol) of 1-benzyl-piperidin-4-yl 4-chloro-benzoate was dissolved in 30 ml of dioxan, filtered over a microfilter and treated with 10 ml of 0.1N HCl. The mixture was stirred for 2 hrs., the solvent was removed completely and the residue was dissolved in 40 ml of water and lyophilized. The lyophilizate was recrystallized from ether/ethanol. 0.278 g (74%) of 1-benzyl-piperidin-4-yl 4-chloro-benzoate hydrochloride (1:1) was obtained as white crystals; m.p. 207°–209°.

EXAMPLE 17

1-Benzyl-piperidin-4-yl 2-bromo-benzoate a) 1.5 g (0.00745 mol) of 2-bromobenzoic acid were dissolved in 25 ml of thionyl chloride under argon and boiled under reflux for 2 hrs. The excess thionyl chloride was distilled off and the residue was taken up twice with 50 ml of toluene and concentrated each time. 1.63 g (100%) of 2-bromobenzoyl chloride were obtained as a yellow solid.

b) 1.79 g (0.0093 mol) of 1-benzyl-4-hydroxypiperidine and 2.3 ml (0.0164 mol) of triethylamine were dissolved in 70 ml of toluene and treated with 1.63 g (0.00745 mol) of 2-bromo-benzoyl chloride. The mixture was boiled at reflux for 6 hrs., the precipitate was filtered off and the filtrate was concentrated. The residue was chromatographed over silica gel with ethyl acetate/hexane (1:2). 1.71 g (61%) of 1-benzyl-piperidin-4-yl 2-bromo-benzoate were obtained as yellowish crystals; m.p. 69°–70°.

c) 0.1 g (0.000267 mol) of 1-benzyl-piperidin-4-yl 2-bromo-benzoate was dissolved in 5 ml of ether and 0.5 ml of methanol and treated with 1 ml of 1N ethereal HCl. The mixture was stirred for 2 hrs. and the resulting precipitate was filtered off, washed with ether and dried. 0.085 g (78%) of 1-benzyl-piperidin-4-yl 2-bromo-benzoate hydrochloride (1:1) was obtained as white crystals; m.p. 205°–206°.

EXAMPLE 18

1-Benzyl-piperidin-4-yl 3-bromo-benzoate a) 0.5 g (0.00216 mol) of 1-benzyl-4-hydroxypiperidine and 0.64 ml (0.0046 mol) of triethylamine were dissolved in 20 ml of toluene and treated with 0.37 ml (0.0027 mol) of 3-bromo-benzoyl chloride. The mixture was boiled at reflux for 6 hrs., the precipitate was filtered off and the filtrate was concentrated. The residue was chromatographed over silica gel with ethyl acetate/hexane (1:3). 0.79 g (98%) of 1-benzyl-piperidin-4-yl 3-bromo-benzoate was obtained as a colorless oil.

b) 0.2 g (0.00053 mol) of 1-benzyl-piperidin-4-yl 3-bromo-benzoate was dissolved in 10 mi of ether and 1 ml of methanol and treated with 5.3ml of 1N ethereal HCl. The mixture was stirred for 2 hrs. and the resulting precipitate was filtered off, washed with ether and dried. 0.2 g (92%) of 1-benzyl-piperidin-4-yl 3-bromo-benzoate hydrochloride (1:1) was obtained as white crystals; m.p. 202°–203°.

EXAMPLE 19

1-Benzyl-piperidin-4-yl 4-bromo-benzoate a) 1.5 g (0.00745 mol) of 4-bromobenzoic acid were dissolved in 25 ml of thionyl chloride under argon and boiled under reflux for 2 hrs. The excess thionyl chloride was distilled off and the residue was taken up twice with 50 ml of toluene and concentrated each time. 1.63 g (100%) of 4-bromobenzoyl chloride were obtained as a yellow solid.

b) 1.79 g (0.00931 mol) of 1-benzyl-4-hydroxy-piperidine and 2.3 ml (0.0164 mol) of triethylamine were dissolved in 20 ml of toluene and treated with 1.63 g (0.00745 mol) of 4-bromobenzoyl chloride. The mixture was boiled at reflux for 6 hrs., the precipitate was filtered off and the filtrate was concentrated. The residue was chromatographed over silica gel with ethyl acetate/hexane (1:2). 2.26 g (81%) of 1-benzyl-piperidin-4-yl 4-bromo-benzoate were obtained as white crystals; m.p. 71°–72°.

c) 2.0 g (0.00534 mol) of 1-benzyl-piperidin-4-yl 4-bromo-benzoate were dissolved in 160 ml of ether and 5 ml of methanol and treated with 20 ml of 1N ethereal HCl. The mixture was stirred for 2 hrs. and the resulting precipitate was filtered off, washed with ether and dried. 1.96 g (89%) of 1-benzyl-piperidin-4-yl 4-bromo-benzoate hydrochloride (1:1) were obtained as white crystals; m.p. 216°–217°.

EXAMPLE 20

1-Benzyl-piperidin-4-yl 2-iodo-benzoate a) 0.75 g (0.00394 mol) of 1-benzyl-4-hydroxy-piperidine and 0.546 ml (0.00394 mol) of triethylamine were dissolved in 50 ml of toluene and treated with 1.0 g (0.00375 mol) of 2-iodo-benzoyl chloride. The mixture was boiled at reflux for 6 hrs., the precipitate was filtered off and the filtrate was concentrated. The residue was chromatographed over silica gel with ethyl acetate/hexane (4:5). 1.05 g (66%) of 1-benzyl-piperidin-4-yl 2-iodo-benzoate were obtained as yellow crystals; m.p. 73°–74°.

b) 0.3 g (0.000712 mol) of 1-benzyl-piperidin-4-yl 2-iodo-benzoate was dissolved in 30 ml of ether and 3 ml of methanol and treated with 1 ml of 1N ethereal HCl. The mixture was stirred for 2 hrs. and the resulting preceipitate was filtered off, washed with ether and dried. 0.3 g (92%) of 1-benzyl-piperidin-4-yl 2-iodo-benzoate hydrochloride (1:1) was obtained as white crystals; m.p. 184°–185°.

EXAMPLE 21

1-Benzyl-piperidin-4-yl 3-iodo-benzoate a) 2.21 g (0.00891 mol) of 3-iodobenzoic acid were dissolved in 25 ml of thionyl chloride under argon and boiled under reflux for 2 hrs. The excess thionyl chloride was distilled off and the residue was taken up twice with 50 ml of toluene and concentrated each time. 1.6 g (67%) of 3-iodobenzoyl chloride were obtained as a yellow solid.

b) 1.21 g (0.0063 mol) of 1-benzyl-4-hydroxypiperidine and 0.874 ml (0.0063 mol) of triethylamine were dissolved in 80 ml of toluene and treated with 1.6 g (0.006 mol) of 3-iodo-benzoyl chloride. The mixture was boiled at reflux for 6 hrs., the precipitate was filtered off and the filtrate was concentrated. The residue was chromatographed over silica gel with ethyl acetate/hexane (1:2). 1.9 g (76%) of 1-benzyl-piperidin-4-yl 3-iodo-benzoate were obtained as yellowish crystals; m.p. 101°–103°.

c) 0.21 g (0.0005 mol) of 1-benzyl-piperidin-4-yl 3-iodo-benzoate was dissolved in 15 ml of ether and 0.75 ml of methanol and treated with 5 ml of 1N ethereal HCl. The mixture was stirred for 2 hrs. and the resulting precipitate was filtered off, washed with ether and dried. 0.189 g (83%) of 1-benzyl-piperidin-4-yl 3-iodobenzoate hydrochloride (1:1) was obtained as white crystals; m.p. 169° (dec.).

EXAMPLE 22

1-Benzyl-piperidin-4-yl 4-iodo-benzoate a) 0.75 g (0.00394 mol) of 1-benzyl-4-hydroxy-piperidine and 0.546 ml (0.00394 mol) of triethylamine were dissolved in 50 ml of toluene and treated with 1.0 g (0.00375 mol) of 4-iodobenzoyl chloride. The mixture was boiled at reflux for 6 hrs., the precipitate was filtered off and the filtrate was concentrated. The residue was chromatographed over silica gel with ethyl acetate/hexane (1:2). 1.07 g (68%) of 1-benzyl-piperidin-4-yl 4-iodo-benzoate were obtained as yellow crystals; m.p. 77°–78°.

b) 0.32 g (0.00076 mol) of 1-benzyl-piperidin-4-yl 4-iodo-benzoate was dissolved in 22.5 ml of ether and 0.75 ml of methanol and treated with 7.5 ml of 1N ethereal HCl. The mixture was stirred for 2 hrs. and the resulting precipitate was filtered off, washed with ether and dried. 0.3 g (85%) of 1-benzyl-piperidin-4-yl 4-iodo-benzoate hydrochloride (1:1) was obtained as white crystals; m.p. 244°–245°.

EXAMPLE 23

1-Benzyl-piperidin-4-yl 3-methyl-benzoate a) 1.0 g (0.00532 mol) of 1-benzyl-4-hydroxypiperidine and 0.72 ml (0.00532 mol) of triethylamine were dissolved in 50 ml of toluene and treated with 0.7 ml (0.00532 mol) of m-toluoyl chloride. The mixture was boiled at reflux for 2 hrs., the precipitate was filtered off and the filtrate was concentrated. The residue was chromatographed over silica gel with ethyl acetate/hexane (1:3→1:2). 1.07 g (65%) of 1-benzyl-piperidin-4-yl 3-methyl-benzoate were obtained as a yellow solid: m.p. 45°–46°.

b) 0.30 g (0.00097 mol) of 1-benzyl-piperidin-4-yl 3-methyl-benzoate was dissolved in 22.5 ml of ether and 0.75 ml of methanol and treated with 7.5 ml of 1N ethereal HCl. The mixture was stirred for 2 hrs. and the resulting precipitate was filtered off, washed with ether and dried. 0.17 g (50%) of 1-benzyl-piperidin-4-yl 3-methyl-benzoate hydrochloride (1:1) was obtained as white crystals; m.p. 209°–211°.

EXAMPLE 24

1-Benzyl-piperidin-4-yl 2-methyl-benzoate a) 1.0 g (0.00532 mol) of 1-benzyl-4-hydroxypiperidine and 0.72 ml (0.00532 mol) of triethylamine were dissolved in 50 ml of toluene and treated with 0.7 ml (0.00532 mol) of o-toluoyl chloride. The mixture was boiled at reflux for 2 hrs., the precipitate was filtered off and the filtrate was concentrated. The residue was chromatographed over silica gel with ethyl acetate/hexane (1:1). 1.3 g (80%) of 1-benzyl-piperidin-4-yl 2-methyl-benzoate were obtained as a brownish oil. MS: me/e (% basic peak)=309 ($C_{20}H_{23}NO_2^+$, 6), 232 (5.5), 173 (22.6), 119 (17.2), 91 (100), 82 (96).

b) 0.30 g (0.00097 mol) of 1-benzyl-piperidin-4-yl 2-methyl-benzoate was dissolved in 22.5 ml of ether and 0.75 ml of methanol and treated with 7.5 ml of 1N ethereal HCl. The mixture was stirred for 2 hrs. and the resulting precipitate was filtered off, washed with ether and dried. 0.25 g (75%) of 1-benzyl-piperidin-4-yl 2-methyl-benzoate hydrochloride (1:1) was obtained as white crystals; m.p. 216°–217°.

EXAMPLE 25

1-Benzyl-piperidin-4-yl 4-methyl-benzoate a) 1.0 g (0.00532 mol) of 1-benzyl-4-hydroxypiperidine and 0.72 ml (0.00532 mol) of triethylamine were dissolved in 50 ml of toluene and treated with 0.7 ml (0.00532 mol) of p-toluoyl chloride. The mixture was boiled at reflux for 2 hrs., the precipitate was filtered off and the filtrate was concentrated. The residue was chromatographed over silica gel with ethyl acetate/hexane (1:3). 1.3 g (80%) of 1-benzyl-piperidin-4-yl 4-methyl-benzoate was obtained as white crystals; m.p. 73°–74°.

b) 0.30 g (0.00097 mol) of 1-benzyl-piperidin-4-yl 4-methyl-benzoate was dissolved in 22.5 ml of ether and 0.75 ml of methanol and treated with 7.5 ml 1N ethereal HCl. The mixture was stirred for 2 hrs. and the resulting precipitate was filtered off, washed with ether and dried. 0.25 g (75%) of 1-benzyl-piperidin-4-yl 4-methyl-benzoate hydrochloride (1:1) was obtained as white crystals; m.p. 216°–218°.

EXAMPLE 26

1-Benzyl-piperidin-4-yl 2-methoxy-benzoate a) 1.41 g (0.00733 mol) of 1-benzyl-4-hydroxypiperidine and 1.8 ml (0.0129 mol) of triethylamine were dissolved in 50 ml of toluene and treated with 0.79 ml (0.00586 mol) of 2-methoxy-benzoyl chloride. The mixture was boiled at reflux for 2 hrs., the precipitate was filtered off and the filtrate was concentrated. The residue was chromatographed over silica gel with ethyl acetate/hexane (1:2). 1.31 g (69%) of 1-benzyl-piperidin-4-yl 2-methoxy-benzoate were obtained as a yellowish oil. MS: me/e=326 ($C_{20}H_{24}NO_3+$).

b) 0.10 g (0.000307 mol) of 1-benzyl-piperidin-4-yl 2-methoxy-benzoate was dissolved in 22.5 ml of ether and 0.75 ml of methanol and treated with 5 ml of 1N ethereal HCl. The mixture was stirred for 2 hrs. and the resulting precipitate was filtered off, washed with ether and dried. 0.08 g (72%) of 1-benzyl-piperidin-4-yl 2-methoxy-benzoate hydrochloride (1:1) was obtained as white crystals; m.p. 176°–177°.

EXAMPLE 27

1-Benzyl-piperidin-4-yl 3-methoxy-benzoate a) 1.41 g (0.00733 mol) of 1-benzyl-4-hydroxypiperidine and 1.8 ml (0.0129 mol) of triethylamine were dissolved in 50 ml of toluene and treated with 0.79 ml (0.00586 mol) of 3-methoxy-benzoyl chloride. The mixture was boiled at reflux for 2 hrs., the precipitate was filtered off and the filtrate was concentrated. The residue was chromatographed over silica gel with ethyl acetate/hexane (1:3→1:2→1:1)). 1.52 g (80%) of 1-benzyl-piperidin-4-yl 3-methoxy-benzoate were obtained as a yellowish oil. MS: me/e (% basic peak)=325 ($C_{20}H_{23}NO_3^+$, 7.6), 248 (4), 173 (30.3), 135 (13), 91 (78), 82 (100).

b) 0.10 g (0.000307 mol) of 1-benzyl-piperidin-4-yl 3-methoxy-benzoate was dissolved in 22.5 ml of ether and 0.75 ml of methanol and treated with 5 ml of 1N ethereal HCl. The mixture was stirred for 2 hrs. and the resulting precipitate was filtered off, washed with ether and dried. 0.09 g (81%) of 1-benzyl-piperidin-4-yl 3-methoxy-benzoate hydrochloride (1:1) was obtained as white crystals; m.p. 177°–178°.

EXAMPLE 28

1-Benzyl-piperidin-4-yl 4-methoxy-benzoate a) 1.41 g (0.00733 mol) of 1-benzyl-4-hydroxypiperidine and 1.8 ml (0.0129 mol) of triethylamine were dissolved in 50 ml of toluene and treated with 0.79 ml (0.00586 mol) of 4-methoxy-benzoyl chloride. The mixture was boiled at reflux for 2 hrs., the precipitate was filtered off and the filtrate was concentrated. The residue was chromatographed over silica gel with ethyl acetate/hexane (1:3→1:2). 0.666 g (35%) of 1-benzyl-piperidin-4-yl 4-methoxy-benzoate was obtained as yellowish crystals; m.p. 55°–56°.

b) 0.10 g (0.000307 mol) of 1-benzyl-piperidin-4-yl 4-methoxy-benzoate was dissolved in 22.5 ml of ether and 0.75 ml of methanol and treated with 5 ml of 1N ethereal HCl. The mixture was stirred for 2 hrs. and the resulting precipitate was filtered off, washed with ether and dried. 0.095 g (85.5%) of 1-benzyl-piperidin-4-yl 4-methoxy-benzoate hydrochloride (1:1) was obtained as white crystals; m.p. 184°–185°.

EXAMPLE 29

1-Benzyl-piperidin-4-yl 4-cyano-benzoate a) 2.0 g (0.01 mol) of 1-benzyl-4-hydroxypiperidine and 1.4 ml (0.01 mol) of triethylamine were dissolved in 100 ml of toluene and treated with 1.6 g (0.00966 mol) of 4-cyanobenzoyl chloride. The mixture was boiled at reflux for 2 hrs., the precipitate was filtered off and the filtrate was concentrated. The residue was chromatographed over silica gel with ethyl acetate/hexane (1:1). 1.9 g (61%) of 1-benzyl-piperidin-4-yl 4-cyano-benzoate were obtained as brownish crystals; m.p. 110°–111°.

b) 0.20 g (0.00065 mol) of 1-benzyl-piperidin-4-yl 4-cyano-benzoate was dissolved in 22.5 ml of ether and 0.75 ml of methanol and treated with 5 ml of 1N ethereal HCl. The mixture was stirred for 2 hrs. and the resulting precipitate was filtered off, washed with ether and dried. 0.185 g (80%) of 1-benzyl-piperidin-4-yl 4-cyano-benzoate hydrochloride (1:1) was obtained as white crystals; m.p. 227°–228°.

EXAMPLE 30

1-Benzyl-piperidin-4-yl 2-methylamino-benzoate a) 0.2 g (0.00064 mol) of 1-benzyl-piperidin-4-yl 2-amino-benzoate was dissolved in 10 ml of acetonitrile and treated with 0.5 ml (0.0064 mol) of formaldehyde (37%) and 0.24 g (0.0032 mol) of NaBH3CN. The pH was adjusted to 6 by the addition of glacial acetic acid. The mixture was stirred at room temperature for 12 hrs., a further 0.15 g of NaBH$_3$CN and 0.2 ml of formaldehyde were then added and the pH was again adjusted to 6 by means of glacial acetic acid. After stirring for a further 2 hrs. the mixture was taken up in 100 ml of ether/water (1:1) and the organic phase was washed twice with saturated bicarbonate solution and once with saturated sodium chloride solution and dried over MgSO$_4$. The residue was chromatographed on silica gel with dichloromethane/methanol (39:1) as the eluent. 0.128 g (61%) of 1-benzyl-piperidin-4-yl 2-methylamino-benzoate was obtained as a colorless oil. MS: m/e=325 ($C_{20}H_{25}N_2O_2$+).

b) 0.12 g (0.00037 mol) of 1-benzyl-piperidin-4-yl 2-methylamino-benzoate was dissolved in 10 ml of ether and 1 ml of methanol and treated with 1 ml of 1N ethereal HCl. The mixture was stirred for 2 hrs. and the resulting precipitate was filtered off, washed with ether and dried. 0.11 g (80%) of 1-benzyl-piperidin-4-yl 2 methylamino-benzoate hydrochloride (1:1) was obtained as white crystals; m.p. 208°–209°.

EXAMPLE 31

1-Benzyl-piperidin-4-yl 3-methylamino-benzoate a) 0.26 g (0.000838 mol) of 1-benzyl-piperidin-4-yl 3-amino-benzoate was dissolved in 8.5 ml of toluene, treated with 0.84 ml (0.0222 mol) of formic acid and boiled at reflux for 12 hrs. The mixture was freed from solvent and the residue was taken up in ethyl acetate and washed with sat. carbonate solution and sodium chloride solution. It was dried over sodium sulfate. 0.26 g (92%) of 1-benzyl-piperidin-4-yl 3-formamido-benzoate was obtained as a brownish oil. MS: m/e=339 ($C_{20}H_{23}N_2O_3$+).

b) 0.253 g (0.00075 mol) of 1-benzyl-piperidin-4-yl 3-formamido-benzoic acid was dissolved in 7.4 ml of THF, treated with 3.4 ml (0.0034 mol) of 1M BH$_3$-THF solution and boiled at reflux for 18 hrs. The reaction mixture was treated with 6.8 ml of 1N aqueous HCl and stirred at room temperature for 1 hr. The mixture was made basic with sat. sodium carbonate solution, extracted with ethyl acetate and the organic phase was subsequently extracted with sat. sodium chloride solution. It was dried over sodium sulfate and concentrated and the residue was chromatographed over silica gel with ethyl acetate/hexane (1:2). 0.13 g (54%) of 1-benzyl-piperidin-4-yl 3-methylamino-benzoate was obtained as a colorless oil. MS: 347 ($C_{20}H_{24}NaN_2O_2$+), 325 ($C_{20}H_{25}N_2O_2$+)

c) 0.124 g (0.00038 mol) of 1-benzyl-piperidin-4-yl 3-methylamino-benzoate was dissolved in 10 ml of ether and 1 ml of methanol, filtered and treated with 3.8 ml of 1N ethereal HCl. The mixture was stirred for 2 hrs., whereby an oil was obtained. The mixture was decanted and the residue was lyophilized. 0.155 g (98%) of 1-benzyl-piperidin-4-yl 3-methylamino-benzoate hydrochloride (1:2.35) was obtained as a white foam. MS: m/e (% basic peak)=324 ($C_{20}H_{24}N_2O_2$$^+$, 11), 247 (3), 172 (40), 91 (90), 82 (100).

EXAMPLE 32

1-Benzyl-piperidin-4-yl 4-methylamino-benzoate a) 0.621 g (0.002 mol) of 1-benzyl-piperidin-4-yl 4-amino-benzoate was suspended in 20 ml of toluene, treated with 2 ml (0.053 mol) of formic acid and boiled at reflux for 8 hrs. The mixture was freed from solvent and the residue was taken up in ethyl acetate and washed with sat. sodium carbonate solution and sodium chloride solution. It was dried over sodium sulfate. 0.586 g (100%) of 1-benzyl-piperidin-4-yl 4-formamido-benzoate was obtained as an amorphous, white substance. MS: m/e=339 ($C_{20}H_{23}N_2O_3$+).

b) 0.338 g (0.001 mol) of 1-benzyl-piperidin-4-yl 4-formamido-benzoate was dissolved in 10 ml of THF, treated with 4.5 ml (0.0045 mol) of 1M BH$_3$-THF solution and boiled at reflux for 18 hrs. The reaction mixture was treated with 9 ml of 1N aqueous HCl and stirred at room temperature for 1 hr. The mixture was made basic with sat. sodium carbonate solution, extracted with ethyl acetate and the organic phase was subsequently extracted with sat. sodium chloride solution. It was dried over sodium sulfate and concentrated and the residue was chromatographed over silica gel with ethyl acetate/toluene (1:2). 0.105 g (32%) of 1-benzyl-piperidin-4-yl 4-methylamino-benzoate was obtained as a colorless oil.

c) 0.10 g (0.00031 mol) of 1-benzyl-piperidin-4-yl 4-methylamino-benzoate was dissolved in 10 ml of ether and 1 ml of methanol, filtered and treated with 3.1 ml of 1N ethereal HCl. The mixture was stirred at room temperature for 12 hrs. and the precipitate was filtered off and dried in a high vacuum. 0.095 g (79%) of 1-benzyl-piperidin-4-yl 4-methylamino-benzoate hydrochloride (1:1.6) was obtained as white crystals; m.p. 168°–170° (dec.).

EXAMPLE 33

1-Benzyl-piperidin-4-yl 2-dimethylamino-benzoate a) 0.33 g (0.002 mol) of 2-dimethylaminobenzoic acid was dissolved in 10 ml of dimethylformamide, treated with 0.122 g (0.001 mol) of dimethylaminopyridine and 0.383 g (0.002 mol) of 1-benzyl-4-hydroxypiperidine and cooled to 0°. 0.422 g (0.0022 mol) of N-ethyl-N'-(3-dimethylaminopropyl)-carbodiimide hydrochloride was added and the mixture was stirred at 0° for a further 2 hrs. Subsequently, the mixture was stirred at room temperature for 3 days, the solvent was distilled off and the residue was chromatographed on silica gel with ethyl acetate/hexane (1:2). 0.31 g (46%) of 1-benzyl-piperidin-4-yl 2-dimethylamino-benzoate was obtained as a colorless oil.

b) 0.30 g (0.000886 mol) of 1-benzyl-piperidin-4-yl 2-dimethylamino-benzoate was dissolved in 27 ml of ether, filtered, diluted with 5 ml of methanol and treated with 3.1 ml of 1N ethereal HCl. The mixture was stirred at room temperature for 2 hrs. and the precipitate was filtered off and dried in a high vacuum. 0.18 g (49%) of 1-benzyl-piperidin-4-yl 2-dimethyl-amino-benzoate hydrochloride (1:2) was obtained as white crystals; m.p. 213°–214° (dec.).

EXAMPLE 34

1-Benzyl-piperidin-4-yl 3-dimethylamino-benzoate a) 0.33 g (0.002 mol) of 3-dimethylaminobenzoic acid was dissolved in 10 ml of dimethylformamide, treated with 0.122 g (0.001 mol) of dimethylaminopyridine and 0.383 g (0.002 mol) of 1-benzyl-4-hydroxypiperidine and cooled to 0°. 0.422 g (0.0022 mol) of N-ethyl-N'-(3-dimethylaminopropyl)-carbodiimide hydrochloride was added and the mixture was stirred at 0° for a further 2 hrs. Subsequently, the mixture was stirred at room temperature for 3 days, the solvent was distilled off and the residue was chromatographed over silica gel with ethyl acetate/hexane (1:2). 0.454 g (67%) of 1-benzyl-piperidin-4-yl 3-dimethylamino-benzoate was obtained as a colorless oil.

b) 0.254 g (0.000751 mol) of 1-benzyl-piperidin-4-yl 3-dimethylaminobenzoate was dissolved in 23 ml of ether, filtered, diluted with 0.7 ml of methanol and treated with 7.5 ml of 1N ethereal HCl. The mixture was stirred at room temperature for 2 hrs. and the precipitate was filtered off and dried in a high vacuum. 0.28 g (91%) of 1-benzyl-piperidin-4-yl 3-dimethyl-amino-benzoate hydrochloride (1:1.95) was obtained as white crystals; m.p. 226°–228° (dec.).

EXAMPLE 35

1-Benzyl-piperidin-4-yl 4-dimethylamino-benzoate a) 0.1025 g (0.00033 mol) of 1-benzyl-piperidin-4-yl 4-amino-benzoate was dissolved in 5 ml of acetonitrile and treated with 0.4 ml (0.0053 mol) of formaldehyde (37%) and 0.113 g (0.001534 mol) of NaBH$_3$CN. The pH was adjusted to 6 with glacial acetic acid and the reaction mixture was stirred at 50° for 1 hr. Subsequently, the mixture was diluted with 25 ml of ether, washed with saturated bicarbonate solution and saturated sodium chloride solution and the org. phase was dried over magnesium sulfate. After removing the solvent the residue was chromatographed over silica gel with dichloromethane/methanol (19:1). 0.078 g (70%) of 1-benzyl-piperidin-4-yl 4-dimethylamino-benzoate was obtained as white crystals; m.p. 103°.

b) 0.06 g (0.000177 mol) of 1-benzyl-piperidin-4-yl 4-dimethylaminobenzoate was dissolved in 10 ml of ether, filtered, diluted with 1 ml of methanol and treated with 1 ml of 1N ethereal HCl. The mixture was stirred at room temperature for 2 hrs. and the precipitate was filtered off and dried in a high vacuum. 0.05 g (69%) of 1-benzyl-piperidin-4-yl 4-dimethyl-amino-benzoate hydrochloride (1:2) was obtained as white crystals. MS: me/e (% basic peak)=338 ($C_{21}H_{26}N_2O_2^+$, 10), 173 (96.6), 148 (27.6), 91 (100), 82 (85.5).

EXAMPLE 36

1-Benzyl-piperidin-4-yl 2-nitro-4-trifluoromethyl-benzoate a) 0.56 g (0.00238 mol) of 2-nitro-4-trifluoromethyl-benzoic acid was dissolved in 7 ml of thionyl chloride and boiled under reflux for 2 hrs. The reaction mixture was concentrated and the residue was taken up twice in toluene and evaporated to dryness each time. 0.53 g (94%) of 2-nitro-4-trifluoromethyl-benzoyl chloride was obtained as a yellow oil.

b) 0.537 g (0.00279 mol) 1-benzyl-4-hydroxypiperidine and 0.69 ml (0.0049 mol) of triethylamine were dissolved in 20 ml of toluene and treated with 0.53 g (0.00223 mol) of 2-nitro-4-trifluoromethyl-benzoyl chloride in 5 ml of toluene. The mixture was boiled at reflux for 6 hrs., the precipitate was filtered off and the filtrate was concentrated. The residue was chromatographed over silica gel with ethyl acetate/hexane (1:1). 0.79 g (86%) of 1-benzyl-piperidin-4-yl 2-nitro-4-trifluoro-methyl-benzoate was obtained as yellow crystals; m.p. 78°–79°.

c) 0.1 g (0.000245 mol) of 1-benzyl-piperidin-4-yl 2-nitro-4-trifluoromethyl-benzoate was dissolved in 10 ml of ether and 1 ml of methanol and treated with 1 ml of 1N ethereal HCl. The mixture was stirred for 2 hrs. and the resulting precipitate was filtered off, washed with ether and dried. 0.09 g (83%) of 1-benzyl-piperidin-4-yl 2-nitro-4-trifluoromethyl-benzoate hydrochloride (1:1) was obtained as white crystals; m.p. 207°–208°.

EXAMPLE 37

1-Benzyl-piperidin-4-yl 2-amino-4-trifluoromethyl-benzoate a) 0.25 g (0.000612 mol) of 1-benzyl-piperidin-4-yl 2-nitro-4-trifluoromethyl-benzoate was dissolved in 10 ml of ethanol and treated with 0.15 g of Raney-nickel. The mixture was hydrogenated at room temperature under normal pressure for 2 hrs. The catalyst was filtered off and the solvent was removed completely. The residue was chromatographed over silica gel with ethyl acetate/hexane (1:1) as the eluent. 0.11 g (48%) of 1-benzyl-piperidin-4-yl 2-amino-4-trifluoromethyl-benzoate was obtained as a yellow oil. MS: me/e=379 ($C_{20}H_{22}F_3N_2O_2+$).

b) 0.1 g (0.000238 mol) of 1-benzyl-piperidin-4-yl 2-amino-4-trifluoromethyl-benzoate was dissolved in 5 ml of ether and treated with 3 ml of 1N ethereal HCl. The precipitate was filtered off under suction, washed with ether and recrystallized from ethanol/ether. 0.09 g (91%) of 1-benzyl-piperidin-4-yl 2-amino-4-trifluoromethyl-benzoate hydro-chloride (1:1) was obtained as white crystals; m.p. 117°–119°.

EXAMPLE 38

1-Benzyl-piperidin-4-yl 4-bromo-2-nitro-benzoate a) 0.62 g (0.0025 mol) of 4-bromo-2-nitro-benzoic acid was dissolved in 4 ml of oxalyl chloride and boiled under reflux for 4 hrs. The reaction mixture was concentrated and the residue was taken up twice in toluene and evaporated to dryness each time.

b) 0.482 g (0.0025 mol) of 1-benzyl-4-hydroxypiperidine and 0.62 ml (0.0045 mol) of triethylamine were dissolved in 20 ml of toluene and treated with the 4-bromo-2-nitro-benzoyl chloride obtained under a) dissolved in 5 ml of toluene. The mixture was boiled at reflux for 6 hrs., the precipitate was filtered off and the filtrate was concentrated. The residue was chromatographed over silica gel with ethyl acetate/hexane (1:7 and 1:4). 0.3 g (28%) of 1-benzyl-piperidin-4-yl 4-bromo-2-nitro-benzoate was obtained as a brown oil.

c) 0.084 g (0.0002 mol) of 1-benzyl-piperidin-4-yl 4-bromo-2-nitro-benzoate was dissolved in 6 ml of ether, filtered, diluted with 0.2 ml of methanol and treated with 2 ml of 1N ethereal HCl. After removal of the solvent there remained behind a yellow foam which was dried in a high vacuum. 0.05 g (50%) of 1-benzyl-piperidin-4-yl 4-bromo-2-nitro-benzoate hydrochloride (1:1) was obtained as white crystals; m.p. 90° (dec.).

EXAMPLE 39

1-Benzyl-piperidin-4-yl 2-amino-4-bromo-benzoate a) 0.42 g (0.001 mol) of 1-benzyl-piperidin-4-yl 4-bromo-2-nitro-benzoate was dissolved in 6 ml of ethanol and treated with 6 ml of glacial acetic acid and 0.225 g (0.004 mol) of iron powder. The mixture was boiled at reflux for 6 hrs. and concentrated and the residue was made basic with sat. sodium carbonate solution. The aqueous phase was extracted with ethyl acetate and the organic phase was washed with sat. sodium chloride solution and dried over sodium sulfate. After concentration the residue was chromatographed on silica gel with ethyl acetate/hexane (1:4). 0.415 g (100%) of 1-benzyl-piperidin-4-yl 2-amino-4-bromo-benzoate was obtained as white crystals.

b) 0.41 g (0.001 mol) of 1-benzyl-piperidin-4-yl 2-amino-4-bromo-benzoate was dissolved in 33 ml of ether, filtered, diluted with 3 ml of methanol and treated with 11 ml of 1N ethereal HCl. The mixture was stirred for 2 hrs. The separated precipitate was filtered off and dried in a high vacuum. 0.445 g (96%) of 1-benzyl-piperidin-4-yl 2-amino-4-bromo-benzoate hydrochloride (1:1.95) was obtained as white crystals; m.p. 204°–207°.

EXAMPLE 40

1-Benzyl-piperidin-4-yl 2-amino-4-fluoro-benzoate a) 1.0 g (0.00645 mol) of 2-amino-4-fluoro-benzoic acid was dissolved in 40 ml of dioxan, treated with 0.896 ml (0.009678 mol) of trifluoroacetic anhydride and stirred at room temperature for 19 hrs. The solvent was removed and the residue was dried in a high vacuum.

b) The residue obtained under a) was dissolved in 70 ml of dimethylformamide, treated with 0.457 g (0.00376 mol) of dimethylaminopyridine and cooled to 0°. 1.59 g (0.00828 mol) of N-ethyl-N'-(3-dimethylaminopropyl)-carbodiimide hydrochloride were added and the mixture was stirred at 0° for 2 hrs. Thereafter, the mixture was warmed to room temperature and treated with 1.54 g (0.007526 mol) of 1-benzyl-4-hydroxypiperidine. The mixture was stirred at room temperature for 48 hrs., the solvent was distilled off and the residue was taken up in ethyl acetate and washed with ½ sat. sodium bicarbonate solution. The organic phase was dried over sodium sulfate and concentrated and the residue was chromatographed on silica gel with ethyl acetate/hexane (1:3) as the eluent. 1.145 g (36%) of 1-benzyl-piperidin-4-yl 4-fluoro-2-trifluoroacetamido-benzoate were obtained as a colorless oil.

c) 1.145 g (0.0027 mol) of 1-benzyl-piperidin-4-yl 4-fluoro-2-trifluoroacetamido-benzoate were suspended in 25 ml of 1N aqueous piperidine in an ultrasound bath for ½ hr. and subsequently stirred at room temperature for 48 hrs. The suspension was treated with semi-saturated aqueous sodium chloride solution and extracted with ethyl acetate. The organic phases were dried over sodium sulfate and concentrated and the residue was chromatographed on silica gel with ethyl acetate/hexane (1:3). 0.82 g (92%) of 1-benzyl-piperidin-4-yl 2-amino-4-fluoro-benzoate was obtained as a colorless oil. MS:=329 ($C_{19}H_{22}FN_2O_2+$).

d) 0.565 g (0.00172 mol) of 1-benzyl-piperidin-4-yl 2-amino-4-fluoro-benzoate was dissolved in 30 ml of ether, filtered, diluted with 3 ml of methanol and treated with 10 ml of 1N ethereal HCl. The mixture was stirred for 2 hrs. The separated precipitate was filtered off and dried in a high vacuum. 0.64 g (93%) of 1-benzyl-piperidin-4-yl 2-amino-4-fluoro-benzoate hydrochloride (1:2) was obtained as white crystals; m.p. 193°–196°.

EXAMPLE 41

1-Benzyl-piperidin-4-yl 2-amino-4-chloro-benzoate a) 0.5 g (0.0029 mol) of 2-amino-4-chloro-benzoic acid was dissolved in 20 ml of dioxan, treated with 0.405 ml (0.00437 mol) of trifluoroacetic anhydride and stirred at room temperature for 19 hrs. The solvent was removed and the residue was dried in a high vacuum.

b) The residue obtained under a) was dissolved in 30 ml of dimethylformamide, treated with 0.195 g (0.0016 mol) of dimethylaminopyridine and cooled to 0°. 0.68 g (0.0035 mol) of N-ethyl-N'-(3-dimethylaminopropyl)-carbodiimide hydrochloride was added and the mixture was stirred at 0° for 2 hrs. Thereafter, the mixture was warmed to room temperature and treated with 0.655 g (0.0032 mol) of 1-benzyl-4-hydroxypiperidine. The mixture was stirred at room temperature for 48 hrs., the solvent was distilled off and the residue was taken up in ethyl acetate and washed with semi-saturated sodium bicarbonate solution. The organic phase was dried over sodium sulfate and concentrated and the residue was chromatographed on silica gel with ethyl acetate/hexane (1:3) as the eluent. 0.525 g (37%) of 1-benzyl-piperidin-4-yl 4-chloro-2-trifluoroacetamido-benzoate was obtained as a colorless oil.

c) 0.5 g (0.00113 mol) of 1-benzyl-piperidin-4-yl 4-chloro-2-trifluoroacetamido-benzoate was dissolved in 10 ml of 1N aqueous piperidine in an ultrasound bath for ½ hr. and subsequently stirred at room temperature for 48 hrs. The suspension was treated with semi-saturated aqueous sodium chloride solution and extracted with ethyl acetate. The organic phases were dried over sodium sulfate and concentrated and the residue was chromatographed on silica gel with ethyl acetate/hexane (1:2). 0.256 g (65%) of 1-benzyl-piperidin-4-yl 2-amino-4-chloro-benzoate was obtained as a colorless oil. MS: me/e=345 ($C_{19}H_{22}ClN_2O_2+$).

d) 0.11 g (0.00032 mol) of 1-benzyl-piperidin-4-yl 2-amino-4-chloro-benzoate was dissolved in 10 ml of ether, filtered, diluted with 1 ml of methanol and treated with 1 ml of 1N ethereal HCl. The mixture was stirred for 2 hrs. The separated precipitate was filtered off and dried in a high vacuum. 0.05 g (41%) of 1-benzyl-piperidin-4-yl 2-amino-4-chloro-benzoate hydrochloride (1:1) was obtained as white crystals; m.p. 135°–137°.

EXAMPLE 42

1-Benzyl-piperidin-4-yl 4-iodo-2-nitro-benzoate a) 10.0 g (0.06375 mol) of 4-methyl-3-nitroaniline were treated with 50 ml of acetic anhydride at 0° C. After warming to room temperature the mixture was stirred for 1.5 hrs. The precipitate was filtered off, washed with ether and the filtrate was treated with 200 ml of water. The mixture was stirred for a further 2 hrs. and again filtered. The respective precipitates were recrystallized from ethyl acetate/hexane. 11.52 g (93%) of 4-methyl-3-nitroacetanilide were obtained as beige crystals; m.p. 147°–149°.

b) 3.26 g (0.0168 mol) of 4-methyl-3-nitroacetanilide were suspended in 168 ml of water, treated with 2.6 g of $MgSO_4$ and heated to boiling under reflux. A mixture of 13.5 g (0.0855 mol) of potassium permanganate and 3.9 g of $MgSO_4$ was added portionwise within 1 hr. After boiling at reflux for 1 hr. 2 ml of isopropanol were added, the reaction mixture was filtered, the suction filter material was washed with semisaturated bicarbonate solution and the aqueous phase was extracted with 100 ml of ethyl acetate. The aqueous phase was acidified with 37% HCl, cooled in an ice bath and the separated precipitate was filtered off under suction and dried. 2.4 g (61%) of 4-acetamido-2-nitrobenzoic acid were obtained as colorless crystals; m.p. 219°–220°.

c) 3.36 g (0.0185 mol) of 4-acetamido-2-nitrobenzoic acid were dissolved in 34 ml of 10% KOH and stirred at 90° for 1 hr. After cooling to 0° C. the mixture was acidified with 37% HCl, stirred for a further 1 hr., the precipitate was filtered under suction, washed with water and dried in a high vacuum at 45° C. 2.32 g (69%) of 4-amino-2-nitrobenzoic acid were obtained as yellow crystals. MS: me/e=205 ($C_7H_6NaN_2O_4+$).

d) 1.92 g ( 0.0105 mol) of 4-amino-2-nitrobenzoic acid were suspended in 105 ml of water, treated with 2.6 ml of 37% HCl and cooled to 0° C. A solution of 0.87 g (0.0126 mol) of $NaNO_2$ in 2.5 ml of water was added. After stirring for 5 min. a solution of 2.1 g (0.0126 mol) of KI in 3.1 ml of water was added. The reaction mixture was stirred at room temperature for 1 hr. and excess iodine was destroyed with $NaHSO_3$ solution. The mixture was extracted with ethyl acetate and the organic phase was washed with saturated sodium chloride solution and dried over $Na_2SO_4$. After removal of the solvent and drying 1.84 g (60%) of 4-iodo-2-nitrobenzoic acid were obtained as brown crystals. MS: me/e (% basic peak)=292 ($C_7H_3INO_2$—, 78.5), 248 (100).

e) 2.33 g (0.00795 mol) of 4-iodo-2-nitrobenzoic acid were boiled und reflux in 13.8 ml (0.16 mol) of oxalyl chloride for 3 hrs. After removal of the excess oxalyl chloride the mixture was concentrated twice with 30 ml of toluene each time. The residue was dissolved in 80 ml of toluene, treated with 1.94 ml (0.0139 mol) of triethylamine and 1.52 g (0.00795 mol) of 1-benzyl-4-hydroxypiperidine and boiled at reflux for 18 hrs. After removal of the solvent the residue was chromatographed on silica gel with ethyl acetate/hexane (1:3). 0.465 g (13%) of 1-benzyl-piperidin-4-yl 4-iodo-2-nitrobenzoate was obtained as a yellow oil. MS: me/e=467 ($C_{19}H_{20}IN_2O_4+$).

f) 0.093 g (0.0002 mol) of 1-benzyl-piperidin-4-yl 4-iodo-2-nitro-benzoate was dissolved in 10 ml of ether, filtered, diluted with 2 ml of methanol and treated with 2 ml of 1N ethereal HCl. The mixture was stirred for 2 hrs. The separated precipitate was filtered off, heated to reflux in toluene for 5 hr., filtered off under suction and dried in high vacuum. 07 g (70%) of 1-benzyl-piperidin-4-yl 4-iodo-2-nitro-benzoate hydrochloride (1:1) was obtained as yellowish crystals; m.p. 204°–207°.

EXAMPLE 43

1-Benzyl-piperidin-4-yl 4-iodo-2-amino-benzoate a) 0.26 g (0.000588 mol) of 1-benzyl-piperidin-4-yl 4-iodo-2-nitro-benzoate was dissolved in 3.3 ml of ethanol, diluted with 3.3 ml of acetic acid and treated with 0.123 g (0.0022 mol) of iron powder. The mixture was boiled at reflux for 4 hrs., the solvent was distilled off, the residue was taken up in ethyl acetate, washed with saturated sodium carbonate solution and sodium chloride solution and the organic phase was dried over sodium sulfate. The residue was chromatographed on silica gel with ethyl acetate/hexane (1:4) as the eluent. 0.232 g (95%) of 1-benzyl-piperidin-4-yl 4-iodo-2-amino-benzoate was obtained as a yellow oil. MS: me/e=437 ($C_{19}H_{22}IN_2O_2+$).

b) 0.29 g (0.000665 mol) of 1-benzyl-piperidin-4-yl 4-iodo-2-amino-benzoate was dissolved in 1.3 ml of methanol, treated with 6.7 ml of 1M ethereal HCl and stirred for 10 min. The mixture was concentrated, the residue was taken up in 10 ml of methanol and cooled. The precipitate which separated after a short time was filtered off under suction, washed with a small amount of methanol and dried at 45° in a high vacuum. 0.1 g (30%) of 1-benzyl-piperidin-4-yl 4-iodo-2-amino-benzoate hydro-chloride (1:2) was obtained as colorless crystals; m.p. 221°–223°.

EXAMPLE 44

1-Benzyl-piperidin-4-yl 2,4-diamino-benzoate a) 0.546 g (0.003 mol) of 2-amino-4-nitro-benzoic acid were dissolved in 30 ml of dioxan, treated with 0.52 ml (0.00375 mol) of trifluoroacetic anhydride and stirred at room temperature for 19 hrs. The solvent was removed, the residue was triturated in 20 ml of ether, filtered off over a frit and dried in a high vacuum. 0.4 g (48%) of 4-nitro-2-trifluoro-acetamido-benzoic acid was obtained as brown crystals; m.p. 183°–185°.

b) 0.39 g (0.0014 mol) of 4-nitro-2-trifluoroacetamido-benzoic acid was dissolved in 7 ml of dimethylformamide, treated with 0.0855 g (0.0007 mol) of dimethylaminopyridine and cooled to 0°. 0.268 g (0.0014 mol) of 1-benzyl-4-hydroxy-piperidine and 0.295 g (0.00154 mol) of N-ethyl-N'-(3-dimethylaminopropyl)-carbodiimide hydrochloride were added and the mixture was stirred at 0° for 2 hrs. Thereafter, the mixture was warmed to room temperature. The mixture was stirred at room temperature for 48 hrs., the solvent was distilled off and the residue was taken up in ethyl acetate and washed with semi-saturated sodium bicarbonate solution. The organic phase was dried over sodium sulfate and concentrated and the residue was chromatographed on silica gel with ethyl acetate/hexane (1:2) as the eluent. 0.28 g (44%) of 1-benzyl-piperidin-4-yl 4-nitro-2-trifluoroacetamido-benzoate was obtained as a yellow oil. MS: me/e=452 ($C_{21}H_{21}F_3N_3O_5+$).

c) 0.275 g (0.00061 mol) of 1-benzyl-piperidin-4-yl 4-nitro-2-trifluoroacetamido-benzoate was suspended in 12 ml of 1N aqueous piperidine in an ultrasound bath for ½ hr. and subsequently stirred at room temperature for 20 hrs. The suspension was treated with semi-saturated aqueous sodium chloride solution and extracted with ethyl acetate. The organic phases were dried over sodium sulfate, concentrated and chromatographed on silica gel with ethyl acetate/hexane (1:2). 0.20 g (92%) of 1-benzyl-piperidin-4-yl 2-amino-4-nitro-benzoate was obtained as a yellow oil. MS: me/e=356 ($C_{19}H_{22}N_3O_4+$).

d) 0.19 g (0.000537 mol) of 1-benzyl-piperidin-4-yl 2-amino-4-nitro-benzoate was dissolved in 16 ml of ethanol, treated with 0.115 g of Raney-Nickel and hydrogenated under normal pressure. The catalyst was filtered off, the solvent was removed on a rotary evaporator and the residue was chromatoraphed on silica gel with ethyl acetate/hexane (1:1→1:1) as the eluent. 0.155 g (89%) of 1-benzyl-piperidin-4-yl 2,4-diamino-benzoate was obtained as white crystals.

e) 0.152 g (0.000467 mol) of 1-benzyl-piperidin-4-yl 2,4-diamino-benzoate was dissolved in 14 ml of ether, filtered, diluted with 0.5 ml of methanol and treated with 5 ml of 1N ethereal HCl. The mixture was stirred for 2 hrs. The separated precipitate was filtered off, recrystallized from ether/ethanol and dried in a high vacuum. 0.135 g (74%) of 1-benzyl-piperidin-4-yl 2,4-diamino-benzoate hydrochloride (1:1.85) was obtained as white crystals; m.p. 220°–230°.

EXAMPLE 45

1-Benzyl-piperidin-4-yl 2-amino-4-methyl-benzoic acid a) 0.756 g (0.005 mol) of 2-amino-4-methylbenzoic acid was dissolved in 50 ml of dioxan, treated with 0.87 ml (0.00625 mol) of trifluoroacetic anhydride and stirred at room temperature for 16 hrs. The solvent was removed and the residue was triturated in a mixture of 40 ml of hexane and 4 ml of ether, filtered off over a frit and dried in a high vacuum. 1.15 g (93%) of 4-methyl-2-trifluoroacetamido-benzoic acid were obtained as beige crystals; m.p. 178°–180°.

b) 1.12 g (0.00453 mol) of 4-methyl-2-trifluoroaceta-mido-benzoic acid were dissolved in 23 ml of dimethylformamide, treated with 0.277 g (0.00227 mol) of dimethylaminopyridine and cooled to 00. 0.867 g (0.00453 mol) of 1-benzyl-4-hydroxy-piperidine and 0.955 g (0.005 mol) of N-ethyl-N'-(3-dimethylaminopropyl)-carbodiimide hydrochloride were added and the mixture was stirred at 0° for 2 hrs. Thereafter, the mixture was warmed to room temperature. The mixture was stirred at room temperature for 48 hrs., the solvent was distilled off and the residue was taken up in ethyl acetate and washed with semi-sat. sodium bicarbonate solution. The organic phase was dried over sodium sulfate and concentrated and the residue was chromatographed on silica gel with ethyl acetate/hexane (1:2) as the eluent. 1.27 g (77%) of 1-benzyl-piperidin-4-yl 4-methyl-2-trifluoroacetamido-benzoate were obtained as a yellow oil. MS: me/e=421 ($C_{22}H_{24}F_3N_2O_3+$).

c) 1.22 g (0.0029 mol) of 1-benzyl-piperidin-4-yl 4-methyl-2-trifluoroacetamido-benzoate were suspended in 60 ml of 1N aqueous piperidine in an ultrasound bath for ½ hr., treated with 10 ml of dioxan and subsequently stirred at room temperature for 20 hrs. Subsequently, the mixture was heated to 50° for 5 hrs. The suspension was treated with saturated aqueous sodium chloride solution and extracted with ethyl acetate. The organic phases were dried over sodium sulfate and concentrated and the residue was chromatographed on silica gel with ethyl acetate/hexane (1:2). 0.82 g (87%) of 1-benzyl-piperidin-4-yl 2-amino-4-methyl-benzoate was obtained as a colorless oil.

d) 0.81 g (0.0025 mol) of 1-benzyl-piperidin-4-yl 2-amino-4-methyl-benzoate was dissolved in 75 ml of ether, filtered, diluted with 2.5 ml of methanol and treated with 12.5 ml of 1N ethereal HCl. The mixture was stirred for 2 hrs. The separated precipitate was filtered off, recrystallized from ether/ethanol and dried in a high vacuum. 0.92 g (93%) of 1-benzyl-piperidin-4-yl 2-amino-4-methyl-benzoate hydrochloride (1:1.95) was obtained as white crystals; m.p. 223°–226° (dec.).

EXAMPLE 46

1-Benzyl-piperidin-4-yl 2,4-dimethyl-benzoate a) 0.45 g (0.003 mol) of 2,4-dimethylbenzoic acid were boiled under reflux in 5.2 ml (0.06 mol) of oxalyl chloride for 3 hrs. After removal of the excess oxalyl chloride the mixture was concentrated twice with 5 ml of toluene each time. The residue was dissolved in 20 ml of toluene, treated with 0.74 ml (0.0053 mol) of triethylamine and 0.574 g (0.003 mol) of 1-benzyl-4-hydroxypiperidine and boiled at reflux for 18 hrs. After removal of the solvent the residue was chromatographed on silica gel with ethyl acetate/hexane (1:3). 0.805 g (83%) of 1-benzyl-piperidin-4-yi 2,4-dimethyl-benzoate was obtained as a yellow oil. MS: me/e= 324 ($C_{21}H_{26}NO_2+$).

b) 0.79 g (0.00244 mol) of 1-benzyl-piperidin-4-yl 2,4-dimethyl-benzoate was dissolved in 73 ml of ether, filtered, diluted with 5 ml of methanol and treated with 12 ml of 1N ethereal HCl. The mixture was stirred for 2 hrs. The separated precipitate was filtered off and dried in a high vacuum. 0.62 g (71%) of 1-benzyl-piperidin-4-yl 2,4-dimethyl-benzoate hydrochloride (1:1) was obtained as white crystals; m.p. 201°–202°.

EXAMPLE 47

1-Benzyl-piperidin-4-yl 4-bromo-2-methyl-benzoate a) 2.0 g (0.0093 mol) of 4-bromo-2-methylbenzoic acid were boiled under reflux in 15 ml (0.175 mol) of oxalyl chloride for 3 hrs. After removal of the excess oxalyl chloride the mixture was concentrated twice with 10 ml of toluene each time. The residue was dissolved in 15 ml of toluene, treated with 2.33 ml (0.01675 mol) of triethylamine and 2.67 g (0.01395 mol) of 1-benzyl-4-hydroxypiperidine and boiled at reflux for 18 hrs. After removal of the solvent the residue was chromatographed on silica gel with ethyl acetate/hexane (1:3). 2.12 g (59%) of 1-benzyl-piperidin-4-yl 4-bromo-2-methyl-benzoate were obtained as a yellow oil.

b) 2.11 g (0.0054 mol) of 1-benzyl-piperidin-4-yl 4-bromo-2-methyl-benzoate were dissolved in 163 ml of ether, filtered, diluted with 16 ml of methanol and treated with 54 ml of 1N ethereal HCl. The mixture was stirred for 2 hrs. The separated precipitate was filtered off and dried in a high vacuum. 1.44 g (63%) of 1-benzyl-piperidin-4-yl 4-bromo-2-methyl- benzoate hydrochloride (1:1) were obtained as white crystals; m.p. 205°–207°.

EXAMPLE 48

1-(2-Bromo-benzyl)-piperidin-4-yl benzoate a) 0.202 g (0.002 mol) of 4-hydroxypiperidine and 0.55 g (0.0022 mol) of 2-bromobenzyl bromide were dissolved in 5 ml of dimethylformamide and stirred at room temperature for 2 hrs. The solvent was distilled off and the residue was taken up in dichloromethane and washed with sat. bicarbonate solution and sodium chloride solution. The organic phase was dried over sodium sulfate and concentrated. 0.52 g (96%) of 1-(2-bromo-benzyl)-piperidin-4-ol was obtained as a brown oil. MS: me/e (% basic peak)=271, 269 ($C_{12}H_{16}BrNO+$, 53, 56), 270, 268 (66, 60), 171, 169 (86, 88), 114 (100), 100 (77).

b) 0.108 g (0.0004 mol) of 1-(2-bromo-benzyl)-piperidin-4-ol and 0.12 ml (0.00085 mol) of triethylamine were dissolved in 4 ml of toluene, treated with 0.058 ml (0.0005 mol) of benzoyl chloride and boiled at reflux for 18 hrs. The reaction mixture was concentrated and the residue was chromatographed over silica gel with ethyl acetate/hexane (1:1). 0.106 g (71%) of 1-(2-bromo-benzyl)-piperidin-4-yl benzoate was obtained as a colorless oil.

c) 0.104 g (0.000278 mol) of 1-(2-bromo-benzyl)-piperidin-4-yl benzoate was dissolved in 8.5 ml of ether, filtered, diluted with 0.3 ml of methanol and treated with 2.8 ml of 1N ethereal HCl. The separated precipitate was filtered off and dried. 0.093 g (82%) of 1-(2-bromo-benzyl)-piperidin-4-yl benzoate hydrochloride (1:1) was obtained as white crystals; m.p. 190°–192°.

EXAMPLE 49

1-(2-Bromo-benzyl)-piperidin-4-yl 4-methyl-benzoate a) 0.54 g (0.002 mol) of 1-(2-bromo-benzyl)-piperidin-4-ol and 1.23 ml (0.0088 mol) of triethylamine were dissolved in 4 ml of toluene, treated with 0.058 ml (0.0005 mol) of p-toluoyl chloride and boiled at reflux for 18 hrs. The reaction mixture was concentrated and the residue was chromatographed over silica gel with ethyl acetate/hexane (1:3). 0.463 g (60%) 1-(2-bromo-benzyl)-piperidin-4-yl 4-methyl-benzoate was obtained as a colorless oil.

b) 0.463 g (0.0012 mol) of 1-(2-bromo-benzyl)-piperidin-4-yl 4-methyl-benzoate was dissolved in 36 ml of ether, filtered, diluted with 1.8 ml of methanol and treated with 18 ml of 1N ethereal HCl. The separated precipitate was filtered off and dried. 0.375 g (74%) of 1-(2-bromo-benzyl)-piperidin-4-yl 4-methyl-benzoate hydrochloride (1:1) was obtained as white crystals; m.p. 194°–196°.

EXAMPLE 50

1-(3-Bromo-benzyl)-piperidin-4-yl benzoate a) 0.202 g (0.002 mol) of 4-hydroxypiperidine and 0.55 g (0.0022 mol) of 3-bromobenzyl bromide were dissolved in 5 ml of dimethylformamide and stirred at room temperature for 2 hrs. The solvent was distilled off and the residue was taken up in dichloromethane and washed with saturated bicarbonate solution and sodium chloride solution. The organic phase was dried over sodium sulfate and concentrated. 0.52 g (96%) 1-(3-bromo-benzyl)-piperidin-4-ol was obtained as a brown oil. MS: me/e (% basic peak)=271, 269 ($C_{12}H_{16}BrNO^+$, 26, 26.6), 270, 268 (25.5, 22), 171, 169 (47, 48.3), 114 (76.6), 100 (100).

b) 0.108 g (0.0004 mol) of 1-(3-bromo-benzyl)-piperidin-4-ol and 0.12 ml (0.00085 mol) of triethylamine were dissolved in 4 ml of toluene, treated with 0.058 ml (0.0005 mol) of benzoyl chloride and boiled at reflux for 18 hrs. The reaction mixture was concentrated and the residue was chromatographed over silica gel with ethyl acetate/hexane (1:1). 0.08 g (53.5%) of 1-(3-bromo-benzyl)-piperidin-4-yl benzoate was obtained as a colorless oil.

c) 0.074 g (0.000198 mol) of 1-(3-bromo-benzyl)-piperidin-4-yl benzoate was dissolved in 6 ml of ether, filtered, diluted with 0.2 ml of methanol and treated with 2 ml of 1N ethereal HCl. The separated precipitate was filtered off and dried. 0.065 g (80%) of 1-(3-bromo-benzyl)-piperidin-4-yl benzoate hydrochloride (1:1) was obtained as white crystals; m.p. 228–230°.

EXAMPLE 51

1-(3-Bromo-benzyl)-piperidin-4-yl 4-methyl-benzoate a) 0.38 g (0.001.41 mol) of 1-(3-bromo-benzyl)-piperidin-4-ol and 0.49 ml (0.0035 mol) of triethylamine were dissolved in 4 ml of toluene, treated with 0.23 ml (0.00176 mol) of p-toluoyl chloride and boiled at reflux for 18 hrs. The reaction mixture was concentrated and the residue was chromatographed over silica gel with ethyl acetate/hexane (1:4). 0.358 g (65%) of 1-(3-bromo-benzyl)-piperidin-4-yl 4-methyl-benzoate was obtained as a yellow oil.

b) 0.353 g (0.0009 mol) of 1-(3-bromo-benzyl)-piperidin-4-yl 4-methyl-benzoate was dissolved in 28 ml of ether, filtered, diluted with 0.83 ml of methanol and treated with 8.3 ml of 1N ethereal HCl. The separated precipitate was filtered off and dried. 0.28 g (73%) of 1-(3-bromo-benzyl)-piperidin-4-yl 4-methyl-benzoate hydrochloride (1:1) was obtained as white crystals; m.p. 232° (dec.).

EXAMPLE 52

1-(4-Bromo-benzyl)-piperidin-4-yl benzoate a) 0.202 g (0.002 mol) of 4-hydroxypiperidine and 0.55 g (0.0022 mol) of 4-bromobenzyl bromide were dissolved in 5 ml of dimethylformamide and stirred at room temperature for 2 hrs. The solvent was distilled off and the residue was taken up in dichloromethane and washed with sat. bicarbonate solution and sodium chloride solution. The organic phase was dried over sodium sulfate and concentrated. 0.54 g (100%) of 1-(4-bromo-benzyl)-piperidin-4-ol was obtained as a colorless oil. MS: me/e (% basic peak)=271, 269 ($C_{12}H_{16}BrNO^{30}$, 73, 76), 270, 268 (79, 70), 171, 169 (99, 100), 114 (64), 100 (60).

b) 0.108 g (0.0004 mol) of 1-(4-bromo-benzyl)-piperidin-4-ol and 0.12 ml (0.00085 mol) of triethylamine were dissolved in 4 ml of toluene, treated with 0.058 ml (0.0005 mol) of benzoyl chloride and boiled at reflux for 18 hrs. The reaction mixture was concentrated and the residue was chromatographed over silica gel with ethyl acetate/hexane (1:1). 0.125 g (83.5%) of 1-(4-bromo-benzyl)-piperidin-4-yl benzoate was obtained as a colorless oil.

c) 0.121 g (0.000323 mol) of 1-(4-bromo-benzyl)-piperidin-4-yl benzoate was dissolved in 10 ml of ether, filtered, diluted with 0.3 ml of methanol and treated with 3.3 ml of 1N ethereal HCl. The separated precipitate was filtered off and dried. 0.095 g (71.6%) of 1-(4-bromo-benzyl)-piperidin-4-yl benzoate hydrochloride (1:1) was obtained as white crystals; m.p. 235°–237°.

EXAMPLE 53

1-(4-Bromo-benzyl)-piperidin-4-yl 4-methyl-benzoate a) 0.27 g (0.001 mol) of 1-(4-bromo-benzyl)-piperidin-4-ol and 0.346 ml (0.0025 mol) of triethylamine were dissolved in 10 ml of toluene, treated with 0.165 ml (0.00125 mol) of p-toluoyl chloride and boiled at reflux for 18 hrs. The reaction mixture was concentrated and the residue was chromatographed over silica gel with ethyl acetate/hexane (1:5). 0.247 g (64%) of 5 1-(4-bromo-benzyl)-piperidin-4-yl 4-methyl-benzoate was obtained as a yellow oil.

b) 0.242 g (0.0006 mol) of 1-(4-bromo-benzyl)-piperidin-4-yl 4-methyl-benzoate was dissolved in 19 ml of ether, filtered, diluted with 0.95 ml of methanol and treated with 9.54 ml of 1N ethereal HCl. The separated precipitate was filtered off and dried. 0.25 g (94%) of 1-(4-bromo-benzyl)-piperidin-4-yl 4-methyl-benzoate hydrochloride (1:1) was obtained as white crystals; m.p. 230°–244° (dec.).

EXAMPLE 54

1-(2-Chloro-benzyl)-piperidin-4-yl benzoate a) 100 ml of HBr (48%) were heated to 90° and treated portionwise with 1.43 g (0.01 mol) of 2-chlorobenzyl alcohol. The mixture was stirred for ¼ hr. and then cooled to room temperature. The mixture was extracted with ethyl acetate and the organic phase was washed with water and saturated sodium chloride solution and dried over sodium sulfate. 1.75g (85%) of 2-chlorobenzyl bromide were obtained as a slightly turbid, colorless oil; b.p. 130°/30 mmHg.

b) 0.202 g (0.002 mol) of 4-hydroxypiperidine, 1.22 ml (0.0088 mol) of triethylamine and 0.43 g (0.0021 mol) of 2-chlorobenzyl bromide were dissolved in 5 ml of dimethylform-amide and stirred at room temperature for 2 hrs. The solvent was distilled off and the residue was taken up in dichloromethane and washed with saturated bicarbonate solution and sodium chloride solution. The organic phase was dried over sodium sulfate and concentrated. 0.28 g (62%) 1-(2-chloro-benzyl)-piperidin-4-ol was obtained as a colorless oil.

c) 0.14 g (0.00062 mol) of 1-(2-chloro-benzyl)-piperidin-4-ol and 0.17 ml (0.00123 mol) of triethylamine were dissolved in 6.2 ml of toluene, treated with 0.09 ml (0.000776 mol) of benzoyl chloride and boiled at reflux for 18 hrs. The reaction mixture was concentrated and the residue was chromatographed over silica gel with ethyl acetate/hexane (1:1→1:2). 0.16 g (78%) of 1-(2-chloro-benzyl)-piperidin-4-yl benzoate was obtained as a colorless oil.

d) 0.155 g (0.00047 mol) of 1-(2-chloro-benzyl)-piperidin-4-yl benzoate was dissolved in 14 ml of ether, filtered, diluted with 0.4 ml of methanol and treated with 4.7 ml of 1N ethereal HCl. The separated precipitate was filtered off and dried. 0.16 g (93%) of 1-(2-chloro-benzyl)-piperidin-4-yl benzoate hydrochloride (1:1) was obtained as white crystals;

m.p. 178°–180°.

EXAMPLE 55

1-(2-Chloro-benzyl)-piperidin-4-yl 4-methyl-benzoate a) 0.451 g (0.002 mol) of 1-(2-chloro-benzyl)-piperidin-4-ol and 1.23 ml (0.0088 mol) of triethylamine were dissolved in 4 ml of toluene, treated with 0.331 ml (0.0025 mol) of p-toluoyl chloride and boiled at reflux for 18 hrs. The reaction mixture was concentrated and the residue was chromatographed over silica gel with ethyl acetate/hexane (1:1→1:2). 0.3 g (44%) of 1-(2-chloro-benzyl)-piperidin-4-yl 4-methyl-benzoate was obtained as a colorless oil.

b) 0.298 g (0.000867 mol) of 1-(2-chloro-benzyl)-piperidin-4-yl 4-methyl-benzoate was dissolved in 26 ml of ether, filtered, diluted with 0.8 ml of methanol and treated with 8 ml of 1N ethereal HCl. The separated precipitate was filtered off and dried. 0.285 g (86%) of 1-(2-chloro-benzyl)-piperidin-4-yl 4-methyl-benzoate hydrochloride (1:1) was obtained as white crystals; m.p. 188°–190°.

EXAMPLE 56

1-(3-Chloro-benzyl)-piperidin-4-yl benzoate a) 0.202 g (0.002 mol) of 4-hydroxypiperidine and 0.55 9 (0.0022 mol) of 3-chlorobenzyl bromide were dissolved in 5 ml of dimethylformamide and stirred at room temperature for 2 hrs. The solvent was distilled off and the residue was taken up in dichloromethane and washed with saturated bicarbonate solution and sodium chloride solution. The organic phase was dried over sodium sulfate and concentrated. 0.50 g (99%) of 1-(3-chloro-benzyl)-piperidin-4-ol was obtained as a colorless oil.

b) 0.225 g (0.001 mol) of 1-(3-chloro-benzyl)-piperidin-15 4-ol and 0.61 ml (0.0044 mol) of triethylamine were dissolved in 4 ml of toluene, treated with 0.158 ml (0.0016 mol) of benzoyl chloride and boiled at reflux for 18 hrs. The reaction mixture was concentrated and the residue was chromatographed over silica gel with ethyl acetate/hexane (1:4). 0.314 g (95%) of 1-(3-chloro-benzyl)-piperidin-4-yl benzoate was obtained as a yellowish oil.

c) 0.165 g (0.0005 mol) of 1-(3-chloro-benzyl)-piperidin-4-yl benzoate was dissolved in 15 ml of ether, filtered, diluted with 0.6 ml of methanol and treated with 5 ml of 1N ethereal HCl. The separated precipitate was filtered off and dried. 0.166 g (90.6%) of 1-(3-chloro-benzyl)-piperidin-4-yl benzoate hydrochloride (1:1) was obtained as white crystals; m.p. 227°–228°.

EXAMPLE 57

1-(3-Chloro-benzyl)-piperidin-4-yl 4-methyl-benzoate a) 0.25 g (0.0011 mol) of 1-(3-chloro-benzyl)-piperidin-4-ol and 0.39 ml (0.0028 mol) of triethylamine were dissolved in 11 ml of toluene, treated with 0.184 ml (0.0014 mol) of p-toluoyl chloride and boiled at reflux for 18 hrs. The reaction mixture was concentrated and the residue was chromatographed over silica gel with ethyl acetate/hexane (1:3). 0.155 g (41%) of 1-(3-chloro-benzyl)-piperidin-4-yl 4-methyl-benzoate was obtained as a colorless oil.

b) 0.153 g (0.000445 mol) of 1-(3-chloro-benzyl)-piperidin-4-yl 4-methyl-benzoate was dissolved in 13 ml of ether, filtered, diluted with 0.45 ml of methanol and treated with 1.5 ml of 1N ethereal HCl. The separated precipitate was filtered off and dried. 0.10 g (59%) of 1-(3-chloro-benzyl)-piperidin-4-yl 4-methyl-benzoate hydrochloride (1:1) was obtained as white crystals; m.p. 226°–228°.

EXAMPLE 58

1-(4-Chloro-benzyl)-piperidin-4-yl benzoate a) 100 ml of HBr (48%) were heated to 90° and treated portionwise with 1.43 g (0.01 mol) of 4-chlorobenzyl alcohol. The mixture was stirred for ¼ hr. and then cooled to room temperature. The mixture was extracted with ethyl acetate and the organic phase was washed with water and saturated sodium chloride solution and dried over sodium sulfate. 1.82 g (88.6%) of 4-chloro-benzyl bromide were obtained as colorless crystals; m.p. 53°–55°.

b) 0.202 g (0.002 mol) of 4-hydroxypiperidine, 1.22 ml (0.0088 mol) of triethylamine and 0.43 g (0.0021 mol) of 4-chlorobenzyl bromide were dissolved in 5 ml of dimethylform-amide and stirred at room temperature for 2 hrs. The solvent was distilled off and the residue was taken up in dichloromethane and washed with saturated bicarbonate solution and sodium chloride solution. The organic phase was dried over sodium sulfate and concentrated. 0.50 g (100%) of 1-(4-chloro-benzyl)-piperidin-4-ol was obtained as a colorless oil.

c) 0.225 g (0.001 mol) of 1-(4-chloro-benzyl)-piperidin-4-ol and 0.61 ml (0.0044 mol) of triethylamine were dissolved in 8 ml of toluene, treated with 0.185 ml (0.0016 mol) of benzoyl chloride and boiled at reflux for 18 hrs. The reaction mixture was concentrated and the residue was chromatographed over silica gel with ethyl acetate/hexane (1:3). 0.322 g (98%) of 1-(4-5 chloro-benzyl)-piperidin-4-yl benzoate was obtained as a yellowish oil.

d) 0.165 g (0.0005 mol) of 1-(4-chloro-benzyl)-piperidin-4-yl benzoate was dissolved in 15 ml of ether, filtered, diluted with 0.6 ml of methanol and treated with 5 ml of 1N ethereal HCl. The separated precipitate was filtered off and dried. 0.166 g (90.6%) of 1-(4-chloro-benzyl)-piperidin-4-yl benzoate hydrochloride (1:1) was obtained as white crystals; m.p. 216°–217°.

EXAMPLE 59

1-(4-Chloro-benzyl)-piperidin-4-yl 4-methyl-benzoate a) 0.25 g (0.0011 mol) of 1-(4-chloro-benzyl)-piperidin-4-ol and 0.39 ml (0.0028 mol) of triethylamine were dissolved in 11 ml of toluene, treated with 0.184ml (0.0014mol) of p-toluoyl chloride and boiled at reflux for 18 hrs. The reaction mixture was concentrated and the residue was chromatographed over silica gel with ethyl acetate/ hexane (1:3). 0.135 9 (39%) of 1-(4-chloro-benzyl)-piperidin-4-yl 4-methyl-benzoate was obtained as white crystals.

b) 0.133 g (0.000386 mol) of 1-(4-chloro-benzyl)-30 piperidin-4-yl 4-methyl-benzoate was dissolved in 12 ml of ether, filtered, diluted with 0.4 ml of methanol and treated with 4 ml of of 1N ethereal HCl. The separated precipitate was filtered off and dried. 0.14 g (95%) of 1-(3-chloro-benzyl)-piperidin-4-yl 4-methyl-benzoate hydrochloride (1:1) was obtained as white crystals; m.p. 234°–237°.

EXAMPLE 60

1-(2-Fluoro-benzyl)-piperidin-4-yl benzoate a) 1.28 g (0.0127 mol) of 4-hydroxypiperidine were dissolved in 60 ml of dimethylformamide and cooled to 0°. 3.0 g (0.0159 mol) of 2-fluoro-benzyl bromide and 5.0 ml (0.0349 mol) of triethylamine were added under argon and the mixture was left to come to room temperature. It was stirred for 16 hrs., the solvent was distilled off and the residue was chromatographed on silica gel with dichloromethane/methanol (19:1) as the eluent. 1.76 g (53%) of 2-fluoro-benzyl-piperidin-4-ol were obtained as a yellow oil. MS: me/e=210 ($C_{12}H_{17}FNO^+$).

b) 0.2 g (0.000956 mol) of 1-(2-fluoro-benzyl)-piperidin-4-ol and 0.16 ml (0.00147 mol) of triethylamine were dissolved in 10 ml of toluene, treated with 0.122 ml (0.00105 mol) of benzoyl chloride and boiled at reflux for 18 hrs. The reaction mixture was concentrated and the residue was chromatographed over silica gel with ethyl acetate/ hexane (1:2). 0.17 g (57%) of 1-(2-fluoro-benzyl)-piperidin-4-yl benzoate was obtained as a yellow oil.

c) 0.10 g (0.00032 mol) of 1-(2-fluoro-benzyl)-piperidin-4-yl benzoate was dissolved in 5 ml of ether, filtered, diluted with 0.4 ml of methanol and treated with 3 ml of 1N ethereal HCl. The separated precipitate was filtered off and dried. 0.106 g (95%) of 1-(2-fluoro-benzyl)-piperidin-4-yl benzoate hydrochloride (1:1) was obtained as white crystals; m.p. 222°–223°.

EXAMPLE 61

1-(2-Fluoro-benzyl)-piperidin-4-yl 4-methyl-benzoate a) 0.382 g (0.001825 mol) of 1-(2-fluoro-benzyl)-piperidin-4-ol and 0.512 ml (0.00365 mol) of triethylamine were dissolved in 10 ml of toluene, treated with 0.483 ml (0.00365 mol) of p-toluoyl chloride and boiled at reflux for 18 hrs. The reaction mixture was concentrated and the residue was chromatographed over silica gel with ethyl acetate/hexane (1:2). 0.48 g (80%) of 1-(2-fluoro-benzyl)-piperidin-4-yl 4-methyl-benzoate was obtained as a yellow oil. MS: me/e=328 ($C_{20}H_{23}FNO_2^+$).

b) 0.2 g (0.0006 mol) of 1-(2-fluoro-benzyl)-piperidin-4-yl 4-methyl-benzoate was dissolved in 10 ml of ether, filtered, diluted with 1 ml of methanol and treated with 6 ml of 1N ethereal HCl. The separated precipitate was filtered off and dried. 0.177 g (80%) of 1-(2-fluoro-benzyl)-piperidin-4-yl 4-methyl-benzoate hydrochloride (1:1) was obtained as white crystals; m.p. 195°–196°.

EXAMPLE 62

1-(3-Fluoro-benzyl)-piperidin-4-yl benzoate a) 1.28 g (0.0127 mol) of 4-hydroxypiperidine were dissolved in 60 ml of dimethylformamide and cooled to 0°. 3.0 g (0.0159 mol) of 3-fluoro-benzyl bromide and 5.0 ml (0.0349 mol) of triethylamine were added under argon and the mixture was left to come to room temperature. It was stirred for 16 hrs., the solvent was distilled off and the residue was chromatographed on silica gel with dichloromethane/methanol (19:1) as the eluent. 1.19 g (36%) of 1-(3-fluoro-benzyl)-piperidin-4-ol was obtained as yellow crystals; m.p. 61°–62°.

b) 0.2 g (0.000956 mol) of 1-(3-fluoro-benzyl)-piperidin-4-ol and 0.16 ml (0.00147 mol) of triethylamine were dissolved in 10 ml of toluene, treated with 0.122 ml (0.00105 mol) of benzoyl chloride and boiled at reflux for 18 hrs. The reaction mixture was concentrated and the residue was chromatographed over silica gel with ethyl acetate/ hexane (1:2). 0.2 g (67%) of 1-(3-fluoro-benzyl)-piperidin-4-yl benzoate was obtained as yellow crystals.

c) 0.20 g (0.00064 mol) of 1-(3-fluoro-benzyl)-piperidin-4-yl benzoate was dissolved in 5 ml of ether, filtered, diluted with 0.4 ml of methanol and treated with 3 ml of 1N ethereal HCl. The separated precipitate was filtered off and dried. 0.187 g (83.5%) of 1-(3-fluoro-benzyl)-piperidin-4-yl benzoate hydrochloride (1:1) was obtained as white crystals; m.p. 225°–226°.

EXAMPLE 63

1-(3-Fluoro-benzyl)-piperidin-4-yl 4-methyl-benzoate a) 0.5 g (0.00239 mol) of 1-(3-fluoro-benzyl)-piperidin-4-ol and 0.67 ml (0.00478 mol) of triethylamine were dissolved in 15 ml of toluene, treated with 0.632 ml (0.00478 mol) of p-toluoyl chloride and boiled at reflux for 18 hrs. The reaction mixture was concentrated and the residue was chromatographed over silica gel with ethyl acetate/hexane (1:2). 0.64 g (82%) of 1-(3-fluoro-benzyl)-piperidin-4-yl 4-methyl-benzoate was obtained as a yellow oil. MS: me/e=328 ($C_{20}H_{23}FNO2^+$).

b) 0.2 g (0.0006 mol) of 1-(3-fluoro-benzyl)-piperidin-4-yl 4-methyl-benzoate was dissolved in 10 ml of ether, filtered, diluted with 1 ml of methanol and treated with 6 ml of 1N ethereal HCl. The separated precipitate was filtered off and dried. 0.177 g (80%) of 1-(3-fluoro-benzyl)-piperidin-4-yl 4-methyl-benzoate hydrochloride (1:1) was obtained as white crystals; m.p. 204°–205°.

EXAMPLE 64

1-(4-Fluoro-benzyl)-piperidin-4-yl benzoate a) 0.856 g (0.00846 mol) of 4-hydroxypiperidine was dissolved in 40 ml of dimethylformamide and cooled to 0°.

2.0 g (0.0106 mol) of 4-fluorobenzyl bromide and 3.3 ml (0.0233 mol) of triethylamine were added under argon and the mixture was left to come to room temperature. It was stirred for 16 hrs., the solvent was distilled off and the residue was chromatographed on silica gel with dichloromethane/methanol (17:3) as the eluent. An analytically pure sample was obtained after a second chromatography on silica gel with dichloromethane/methanol (17:3) as the eluent. The remainder was used directly in the next step. 0.176 g (8%) of 1-(4-fluoro-benzyl-piperidin-4-ol was obtained as a yellow oil. MS: me/e=210 ($C_{12}H_{17}FNO^+$).

b) 0.63 g (0.003 mol) of 1-(4-fluoro-benzyl)-piperidin-4-ol and 2.09 ml (0.015 mol) of triethylamine were dissolved in 30 ml of toluene, treated with 1.04 ml (0.009 mol) of benzoyl chloride and boiled at reflux for 18 hrs. The reaction mixture was concentrated and the residue was chromatographed over silica gel with ethyl acetate/hexane (1:3). 0.415 g (44%) of 1-(4-fluoro-benzyl)-piperidin-4-yl benzoate was obtained as a yellow oil. MS: me/e=314 ($C_{19}H_{21}FNO_2^+$).

c) 0.396 g (0.00126 mol) of 1-(4-fluoro-benzyl)-piperidin-4-yl benzoate was dissolved in 35 ml of ether, filtered, diluted with 3 ml of methanol and treated with 15 ml of 1N ethereal HCl. The separated precipitate was filtered off and dried. 0.35 g (79%) of 1-(4-fluoro-benzyl)-piperidin-4-yl benzoate hydrochloride (1:1) was obtained as white crystals;

m.p. 206°–208°.

EXAMPLE 65

1-(4-Fluoro-benzyl)-piperidin-4-yl 4-methyl-benzoate a) 0.5 g (0.00239 mol) of 1-(4-fluoro-benzyl)-piperidin-4-ol and 0.67 ml (0.00478 mol) of triethylamine were dissolved in 15 ml of toluene, treated with 0.632 ml (0.00478 mol) of p-toluoyl chloride and boiled at reflux for 18 hrs. The reaction mixture was concentrated and the residue was chromatographed over silica gel with ethyl acetate/hexane (1:2). 0.355 g (59%) of 1-(4-fluoro-benzyl)-piperidin-4-yl 4-methyl-benzoate was obtained as a yellow oil. MS: me/e=328 ($C_2H_{23}FNO_2^+$).

b) 0.2 g (0.0006 mol) of 1-(4-fluoro-benzyl)-piperidin-4-yl 4-methyl-benzoate was dissolved in 10 ml of ether, filtered, diluted with 1 ml of methanol and treated with 6 ml of 1N ethereal HCl. The separated precipitate was filtered off and dried. 0.177 g (80%) of 1-(4-fluoro-benzyl)-piperidin-4-yl 4-methyl-benzoate hydrochloride (1:1) was obtained as white crystals; m.p. 211°–212°.

EXAMPLE 66

1-(2-Nitro-benzyl)-piperidin-4-yl benzoate a) 0.75 g (0.00741 mol) of 4-hydroxy-piperidine were dissolved in 40 ml of dimethylformamide and cooled to 0°. 3.0 g (0.00926 mol) of 2-nitro-benzyl bromide and 2.87 ml (0.0204 mol) of triethylamine were added under argon and the mixture was left to come to room temperature. It was stirred for 16 hrs., the solvent was distilled off and the residue was taken up in dichloromethane. The organic phase was washed with water and saturated sodium chloride solution, dried over magnesium sulfate and concentrated and the residue was chromatographed on silica gel with dichloromethane/methanol (9:1) as the eluent. 1.22 g (56%) of 1-(2-nitro-benzyl)-piperidin-4-ol were obtained as a yellow oil. MS: me/e=237 ($C_{12}H_{17}N_2O3^+$).

b) 0.5 g (0.00212 mol) of 1-(2-nitro-benzyl)-piperidin-4-ol and 0.595 ml (0.00424 mol) of triethylamine were dissolved in 15 ml of toluene, treated with 0.295 ml (0.00254 mol) of benzoyl chloride and boiled at reflux for 18 hrs. The reaction mixture was concentrated and the residue was chromatographed over silica gel with ethyl acetate/hexane (1:2). 0.484 g (75%) of 1-(2-nitro-benzyl)-piperidin-4-yl benzoate was obtained as a yellow oil. MS: me/e=341 ($C_{19}H_{21}N_2O_4^+$).

c) 0.08 g (0.000235 mol) of 1-(2-nitro-benzyl)-piperidin-4-yl benzoate was dissolved in 4 ml of ether, filtered, diluted with 0.4 ml of methanol and treated with 2.5 ml of 1N ethereal HCl. The separated precipitate was filtered off and dried. 0.053 g (60%) of 1-(2-nitro-benzyl)-piperidin-4-yl benzoate hydrochloride (1:1) was obtained as white crystals; m.p. 216°–217°.

EXAMPLE 67

1-(2-Nitro-benzyl)-piperidin-4-yl 4-methyl-benzoate a) 0.5 g (0.00212 mol) of 1-(2-nitro-benzyl)-piperidin-4-ol and 0.595 ml (0.00424 mol) of triethylamine were dissolved in 15 ml of toluene, treated with 0.561 ml (0.00424 mol) of p-toluoyl chloride and boiled at reflux for 18 hrs. The reaction mixture was concentrated and the residue was chromatographed over silica gel with ethyl acetate/hexane (1:2). 0.696 g (93%) of 1-(2-nitro-benzyl)-piperidin-4-yl 4-methyl-benzoate was obtained as yellow crystals; m.p. 86°–87°.

b) 0.1 g (0.00028 mol) of 1-(2-nitro-benzyl)-piperidin-4-yl 4-methyl-benzoate was dissolved in 5 ml of ether, filtered, diluted with 0.5 ml of methanol and treated with 3 ml of 1N ethereal HCl. The separated precipitate was filtered off and dried. 0.95 g (87%) of 1-(2-nitro-benzyl)-piperidin-4-yl 4-methyl-benzoate hydrochloride (1:1) was obtained as white crystals; m.p. 218°–219°.

EXAMPLE 68

1-(2-Amino-benzyl)-piperidin-4-yl benzoate a) 0.345 g (0.00101 mol) of 1-(2-nitro-benzyl)-piperidin-4-yl benzoate was dissolved in 15 ml of ethanol and treated with 0.2 g of Raney-nickel. The mixture was hydrogenated at room temperature and under normal pressure for 8 hrs. The catalyst was filtered off and, after concentration, the residue was chromatographed on silica gel with ethyl acetate/ hexane (1:3) as the eluent. 0.197 g (61%) of 1-(2-amino-benzyl)-piperidin-4-yl benzoate was obtained as a colorless oil. MS: me/e=311 ($C_{19}H_{23}N_2O_2^+$).

b) 0.189 g (0.00061 mol) of 1-(2-amino-benzyl)-piperidin-4-yl benzoate was dissolved in 18 ml of ether, filtered, diluted with 1.2 ml of methanol and treated with 6 ml of 1N ethereal HCl. The separated precipitate was filtered off and dried. 0.215 g (98%) of 1-(2-amino-benzyl)-piperidin-4-yl benzoate hydrochloride (1:1.85) was obtained as yellowish crystals; m.p. 172° (dec.).

EXAMPLE 69

1-(2-Amino-benzyl)-piperidin-4-yl 4-methyl-benzoate a) 0.32 g (0.0009 mol) of 1-(2-nitro-benzyl)-piperidin-4-yl 4-methyl-benzoate was dissolved in 18 ml of ethanol and treated with 0.192 g of Raney-nickel. The mixture was hydrogenated at room temperature and under normal pressure for 2 hrs. The catalyst was filtered off and, after concentration, the residue was chromatographed on silica gel with ethyl acetate/hexane (1:4) as the eluent. 0.252 g (86%) of 1-(2-amino-benzyl)-piperidin-4-yl 4-methyl-benzoate was obtained as yellowish crystals; m.p. 123°–1250°.

b) 0.247 g (0.000762 mol) of 1-(2-amino-benzyl)-piperidin-4-yl 4-methyl-benzoate was dissolved in 20 ml of ether, filtered, diluted with 5 ml of methanol and treated with 7.5 ml of 1N ethereal HCl. The separated precipitate was filtered off and dried. 0.236 g (78.7%) of 1-(2-amino-benzyl)-piperidin-4-yl 4-methyl-benzoate hydrochloride (1:1.9) was obtained as yellowish crystals; m.p. 190° (dec.).

EXAMPLE 70

1-(3-Nitro-benzyl)-piperidin-4-yl benzoate a) 1.41 g (0.01389 mol) of 4-hydroxypiperidine were dissolved in 60 ml of dimethylformamide and cooled to 0°. 3.0 g (0.01389 mol) of 3-nitrobenzyl bromide and 4.3 ml (0.03056 mol) of triethylamine were added under argon and the mixture was left to come to room temperature. It was stirred for 16 hrs., the solvent was distilled off and the residue was taken up in dichloromethane. The organic phase was washed with water and saturated sodium chloride solution, dried over magnesium sulfate and concentrated and the residue was chromatographed on silica gel with dichloromethane/methanol (19:1) as the eluent. 1.9 g (58%) of 1-(3-nitro-benzyl)-piperidin-4-ol were obtained as a yellow oil. MS: me/e=237 ($C_{12}H_{17}N_2O_3^+$)

b) 0.5 g (0.00212 mol) of 1-(3-nitro-benzyl)-piperidin-4-ol and 0.595 ml (0.00424 mol) of triethylamine were dissolved in 15 ml of toluene, treated with 0.295 ml (0.00254 mol) of benzoyl chloride and boiled at reflux for 18 hrs. The reaction mixture was concentrated and the residue was chromatographed over silica gel with ethyl acetate/hexane (1:2). 0.416 g (58%) of 1-(3-nitro-benzyl)-piperidin-4-yl benzoate was obtained as yellow crystals; m.p. 54°–55°.

c) 0.1 g (0.000294 mol) of 1-(3-nitro-benzyl)-piperidin-4-yl benzoate was dissolved in 5 ml of ether, filtered, diluted with 0.5 ml of methanol and treated with 3 ml of 1N ethereal HCl. The separated precipitate was filtered off and dried. 0.07 g (63%) of 1-(3-nitro-benzyl)-piperidin-4-yl benzoate hydro-chloride (1:1) was obtained as white crystals; m.p. 220°–221°.

EXAMPLE 71

1-(3-Nitro-benzyl)-piperidin-4-yl 4-methyl-benzoate a) 0.65 g (0.00275 mol) of 1-(3-nitro-benzyl)-piperidin-4-ol and 1.9 ml (0.0136 mol) of triethylamine were dissolved in 27.5 ml of toluene, treated with 1.09 ml (0.00825 mol) of 4-methyl-benzoyl chloride and boiled at reflux for 18 hrs. The reaction mixture was concentrated and the residue was chromatographed over silica gel with ethyl acetate/hexane (1:3). 0.715 g (73%) of 1-(3-nitro-benzyl)-piperidin-4-yl 4-methyl-benzoate was obtained as yellow crystals; m.p. 90°–93°.

b) 0.213 g (0.0006 mol) of 1-(3-nitro-benzyl)-piperidin-4-yl 4-methyl-benzoate was dissolved in 23 ml of ether, filtered, diluted with 3 ml of methanol and treated with 6 ml of 1N ethereal HCl. The separated precipitate was filtered off and dried. 0.21 g (90%) of 1-(3-nitro-benzyl)-piperidin-4-yl 4-methyl-benzoate hydrochloride (1:1) was obtained as white crystals; m.p. 229°–231°.

EXAMPLE 72

1-(3-Amino-benzyl)-piperidin-4-yl benzoate a) 0.207 g (0.0006 mol) of 1-(3-nitro-benzyl)-piperidin-4-yl benzoate was dissolved in 12 ml of ethanol and treated with 0.12 g of Raney-nickel. The mixture was hydrogenated at room temperature and under normal pressure for 8 hrs. The catalyst was filtered off and, after concentration, the residue was chromatographed on silica gel with ethyl acetate/hexane (1:1) as the eluent. 0.097 g (52%) of 1-(3-amino-benzyl)-piperidin-4-yl benzoate was obtained as yellowish crystals; m.p. 95°–97°.

b) 0.08 g (0.000258 mol) of 1-(3-amino-benzyl)-piperidin-4-yl benzoate was dissolved in 15 ml of ether, filtered, diluted with 1.5 ml of methanol and treated with 2.6 ml of 1N ethereal HCl. The separated precipitate was filtered off and dried. 0.077 g (78%) of 1-(3-amino-benzyl)-piperidin-4-yl benzoate hydrochloride (1:2) was obtained as white crystals; m.p. 242° (dec.).

EXAMPLE 73

1-(3-Amino-benzyl)-piperidin-4-yl 4-methyl-benzoate a) 0.496 g (0.0014 mol) of 1-(3-nitro-benzyl)-piperidin-4-yl 4-methyl-benzoate was dissolved in 28 ml of ethanol and treated with 0.3 g of Raney-nickel. The mixture was hydrogenated at room temperature and under normal pressure for 4 hrs. The catalyst was filtered off and, after concentration, the residue was chromatographed on silica gel with ethyl acetate/ hexane (1:1→2:1) as the eluent. 0.37 g (81.5%) of 1-(3-amino-benzyl)-piperidin-4-yl 4-methyl-benzoate was obtained as yellowish crystals; m.p. 100°–102°.

b) 0.162 g (0.00.05 mol) of 1-(3-amino-benzyl)-piperidin-4-yl 4-methyl-benzoate was dissolved in 15 ml of ether, filtered, diluted with 2.5 ml of methanol and treated with 5 ml of 1N ethereal HCl. The separated precipitate was filtered off and dried. 0.16 g (80%) of 1-(3-amino-benzyl)-piperidin-4-yl 4-methyl-benzoate hydrochloride (1:2.13) was obtained as white crystals; m.p. 168° (dec.).

EXAMPLE 74

1-(4-Nitro-benzyl)-piperidin-4-yl benzoate a) 1.0 g (0.00989 mol) of 4-hydroxypiperidine was dissolved in 50 ml of dimethylformamide and cooled to 0°. 2.56g (0.001186 mol) of 4-nitro-benzyl bromide and 2.78 ml (0.0198 mol) of triethylamine were added and the mixture was left to come to room temperature. It was stirred for 16 hrs., the solvent was distilled off and the residue was taken up in dichloromethane. The organic phase was washed with water and saturated sodium chloride solution, dried over magnesium sulfate and concentrated and the residue was chromatographed on silica gel with dichloromethane/methanol (9:1) as the eluent. 0.836 g (36%) of 1-(4-nitro-benzyl-piperidin-4-ol was obtained as beige crystals; m.p. 114°–115°.

b) 0.3 g (0.00127mol) of 1-(4-nitro-benzyl)-piperidin-4-ol and 0.356 ml (0.00254 mol) of triethylamine were dissolved in 10 ml of toluene, treated with 0.177 ml (0.0015 mol) of benzoyl chloride and boiled at reflux for 18 hrs. The reaction mixture was concentrated and the residue was chromatographed over silica gel with ethyl acetate/hexane (1:2). 0.335 g (78%) of 1-(4-nitro-benzyl)-piperidin-4-yl benzoate was obtained as yellow crystals. MS: me/e (% basic peak) =340 ($C_{19}H_{20}O_4^+$, 3.5), 235 (5), 218 (41), 105 (26), 82 (100).

c) 0.1 g (0.000294 mol) of 1-(4-nitro-benzyl)-piperidin-5 4-yl benzoate was dissolved in 4 ml of ether, filtered, diluted with 0.4 ml of methanol and treated with 2.5 ml of 1N

41 ethereal HCl. The separated precipitate was filtered off and dried. 0.053 g (60%) of 1-(4-nitro-benzyl)-piperidin-4-yl benzoate hydrochloride (1:1) was obtained as white crystals; m.p. 201°–202°.

EXAMPLE 75

1-(4-Nitro-benzyl)-piperidin-4-yl 4-methyl-benzoate a) 0.5 g (0.00212 mol) of 1-(4-nitro-benzyl)-piperidin-4-ol and 0.595 ml (0.00424 mol) of triethylamine were dissolved in 15 ml of toluene, treated with 0.561 ml (0.00424 mol) of p-toluoyl chloride and boiled at reflux for 18 hrs. The reaction mixture was concentrated and the residue was chromatographed over silica gel with ethyl acetate/hexane (1:2). 0.623 g (83%) of 1-(4-nitro-benzyl)-piperidin-4-yl 4-methyl-benzoate was obtained as yellow crystals. MS: me/e=355 ($C_{20}H_{23}N_2O_4^+$).

b) 0.1 g (0.00028 mol) of 1-(4-nitro-benzyl)-piperidin-4-yl 4-methyl-benzoate was dissolved in 5 ml of ether, filtered, diluted with 0.5 ml of methanol and treated with 3 ml of 1N ethereal HCl. The separated precipitate was filtered off and dried. 0.085 g (78%) of 1-(4-nitro-benzyl)-piperidin-4-yl 4-methyl-benzoate hydrochloride (1:1) was obtained as white crystals; m.p. 212°–213°.

EXAMPLE 76

1-(4-Amino-benzyl)-piperidin-4-yl benzoate a) 0.13 g (0.00038 mol) of 1-(4-nitro-benzyl)-piperidin-4-yl benzoate was dissolved in 7.6 ml of ethanol and treated with 0.08 g of Raney-nickel. The mixture was hydrogenated at room temperature and under normal pressure for 2 hrs. The catalyst was filtered off and, after concentration, the residue was chromatographed on silica gel with ethyl acetate/hexane (1:1) as the eluent. 0.1 g (84%) of 1-(4-amino-benzyl)-piperidin-4-yl benzoate was obtained as a yellowish oil. MS: me/e=311 ($C_{19}H_{23}N_2O_2^+$).

b) 0.093 g (0.0003 mol) of 1-(4-amino-benzyl)-piperidin-4-yl benzoate was dissolved in 9 ml of ether, filtered, diluted with 0.6 ml of methanol and treated with 3 ml of 1N ethereal HCl. The separated precipitate was filtered off and dried. 0.95 g (83%) of 1-(4-amino-benzyl)-piperidin-4-yl benzoate hydrochloride (1:2) was obtained as white crystals; m.p. 218° (dec.).

EXAMPLE 77

1-(4-Amino-benzyl)-piperidin-4-yl 4-methyl-benzoate a) 0.48 g (0.00135 mol) of 1-(4-nitro-benzyl)-piperidin-4-yl 4-methyl-benzoate was dissolved in 27 ml of ethanol and treated with 0.48 g of Raney-nickel. The mixture was hydrogenated at room temperature and under normal pressure for 3 hrs. The catalyst was filtered off and, after concentration, the residue was chromatographed on silica gel with ethyl acetate/hexane (1:1→5:2) as the eluent. 0.405 g (92.5%) of 1-(4-amino-benzyl)-piperidin-4-yl 4-methyl-benzoate was obtained as a yellowish oil. MS: me/e=325 ($C_{20}H_{25}N_2O_2^+$).

b) 0.4 g (0.00123 mol) of 1-(4-amino-benzyl)-piperidin-4-yl 4-methyl-benzoate was dissolved in 4 ml of ethanol, filtered and treated with 12 ml of 1N ethereal HCl. The separated precipitate was filtered off and lyophilized. 0.195 g (40%) of 1-(4-amino-benzyl)-piperidin-4-yl 4-methyl-benzoate hydrochloride (1:2) was obtained as yellow crystals; m.p. 192° (dec.).

42

EXAMPLE 78

1-(4-Methyl-benzyl)-piperidin-4-yl benzoate a) 1.15 g (0.00114 mol) of 4-hydroxypiperidine were dissolved in 15 ml of dimethylformamide and cooled to 0°. 1.92 g (0.001037 mol) of 4-methylbenzyl bromide and 1.59 ml (0.0114 mol) of triethylamine were added under argon and the mixture was left to come to room temperature. It was stirred for 18 hrs., the solvent was distilled off and the residue was taken up in ethyl acetate. The organic phase was washed with water and saturated sodium chloride solution, dried over magnesium sulfate and concentrated and the residue was chromatographed on silica gel with dichloromethane/methanol (9:1) as the eluent. 1.028 g (48%) of 1-(4-methyl-benzyl)-piperidin-4-ol were obtained as beige crystals; m.p. 72°–74°.

b) 0.31 g (0.0015 mol) of 1-(4-methyl-benzyl)-piperidin-4-ol and 0.52 ml (0.00375 mol) of triethylamine were dissolved in 15 ml of toluene, treated with 0.25 ml (0.00215 mol) of benzoyl chloride and boiled at reflux for 18 hrs. The reaction mixture was concentrated and the residue was chromatographed over silica gel with ethyl acetate/hexane (1:4). 0.295 g (64%) of 1-(4-methyl-benzyl)-piperidin-4-yl benzoate was obtained as a yellow oil.

c) 0.28 g (0.0009 mol) 1-(4-methyl-benzyl)-piperidin-4-yl benzoate was dissolved in 45 ml of ether, filtered, diluted with 1.4 ml of methanol and treated with 15 ml of 1N ethereal HCl. The separated precipitate was filtered off and dried. 0.225 g (72%) of 1-(4-methyl-benzyl)-piperidin-4-yl benzoate hydrochloride (1:1) was obtained as white crystals; m.p. 230°–231°.

EXAMPLE 79

1-(4-Methyl-benzyl)-piperidin-4-yl 4-methyl-benzoate a) 0.31 g (0.0015 mol) of 1-(4-methyl-benzyl)-piperidin-4-ol and 0.52 ml (0.00375 mol) of triethylamine were dissolved in 15 ml of toluene, treated with 0.25 ml (0.001875 mol) of p-toluoyl chloride and boiled at reflux for 18 hrs. The reaction mixture was concentrated and the residue was chromatographed over silica gel with ethyl acetate/hexane (1:4). 0.4 g (83%) of 1-(4-methyl-benzyl)-piperidin-4-yl 4-methyl-benzoate was obtained as yellow crystals; m.p. 66°–77°.

b) 0.39 g (0.0012 mol) of 1-(4-methyl-benzyl)-piperidin-4-yl 4-methyl-benzoate was dissolved in 45 ml of ether, filtered, diluted with 1.5 ml of methanol and treated with 15 ml of 1N ethereal HCl. The separated precipitate was filtered off, re-precipitated from ether/methanol and dried. 0.23 g (53%) of 1-(4-methyl-benzyl)-piperidin-4-yl 4-methyl-benzoate hydrochloride (1:1) was obtained as white crystals; m.p. 249°.

EXAMPLE 80

1-(4-Methoxy-benzyl)-piperidin-4-yl benzoate a) 3.0 g (0.0217 mol) of p-methoxybenzyl alcohol were dissolved in 50 ml of ether and treated with 14.4 g (0.0433 mol) of carbon tetrabromide. 11.4 g (0.0433 mol) of triphenyl-phosphine were added while cooling with ice. The mixture was stirred at room temperature for 3 hrs. After removal of the solvent the residue was filtered over a short silica gel column with ether/hexane (1:1) as the eluent. The filtrate was subjected to a bulb-tube distillation. 2.05 g (47%) of 4-methoxybenzyl bromide were obtained as a colorless oil; b.p. 120°–140°(22 Torr). MS: me/e (% basic peak)=202, 200 ($C_8H_9BrO^+$, 3), 121 ($C_8H_9O^+$, 100).

b) 0.97 g (0.00959 mol) of 4-hydroxypiperidine was dissolved in 20 ml of dimethylformamide and cooled to 0°. 1.93 g (0.0096 mol) of 4-methoxybenzyl bromide and 3.0 ml (0.0215 mol) of triethylamine were added under argon and the mixture was left to come to room temperature. It was stirred for 18 hrs., the solvent was distilled off and the residue was taken up in ethyl acetate. The organic phase was washed with water and saturated sodium chloride solution, dried over magnesium sulfate and concentrated and the residue was chromatographed on silica gel with dicloromethane/methanol (19:1) as the eluent. 1.7 g (80%) of 1-(4-methoxy-benzyl)-piperidin-4-ol were obtained as a brown oil. MS: me/e=222 ($C_{13}H_{20}NO_2^+$).

c) 0.52 g (0.0023 mol) of 1-(4-methoxy-benzyl)-piperidin-4-ol was dissolved in 25 ml of dimethylformamide and treated with 0.14 g (0.0012 mol) of dimethylaminopyridine and 0.28 g (0.0023 mol) of benzoic acid. The mixture was cooled to 0° and 0.490 g (0.0025 mol) of N-ethyl-N'-(3-dimethylamino-propyl)-carbodiimide hydrochloride was added. The mixture was warmed to room temperature and stirred for 18 hrs. The solvent was distilled off and the residue was taken up in ethyl acetate and treated with silica gel. After removal of the solvent the residue was chromatographed on silica gel with ethyl acetate/hexane (1:3→1:2) as the eluent. 0.16 g (21%) of 1-(4-methoxy-benzyl)-piperidin-4-yl benzoate was obtained as a yellow oil. MS: me/e=326 ($C_{20}H_{24}NO_3^+$).

d) 0.15 g (0.00046 mol) of 1-(4-methoxy-benzyl)-piperidin-4-yl benzoate was dissolved in 4.5 ml of ether, filtered, diluted with 0.4 ml of methanol and treated with 1.5 ml of 1N ethereal HCl. The separated precipitate was filtered off and dried. 0.131 g (78.7%) of 1-(4-methoxy-benzyl)-piperidin-4-yl benzoate hydrochloride (1:1) was obtained as white crystals; m.p. 226°–227°.

EXAMPLE 81

1-(4-Bromo-benzyl)-piperidin-4-yl 4-chloro-benzoate a) 0.27 g (0.001 mol) of 1-(4-bromo-benzyl)-piperidin-4-ol and 0.359 ml (0.0025 mol) of triethylamine were dissolved in 10 ml of toluene, treated with 0.16 ml (0.00125 mol) of 4-chlorobenzoyl chloride and boiled at reflux for 18 hrs. The reaction mixture was concentrated and the residue was chromatographed over silica gel with ethyl acetate/hexane (1:2). 0.333 g (81.5%) of 1-(4-bromo-benzyl)-piperidin-4-yl 4-chloro-benzoate was obtained as a colorless oil.

b) 0.204 g (0.00055 mol) of 1-(4-bromo-benzyl)-piperidin-4-yl 4-chloro-benzoate was dissolved in 15 ml of ether, filtered, diluted with 0.75 ml of methanol and treated with 5ml of 1N ethereal HCl. The separated precipitate was filtered off and dried. 0.188 g (83.6%) of 1-(4-bromo-benzyl)-piperidin-4-yl 4-chloro-benzoate hydrochloride (1:1) was obtained as white crystals; m.p. 240°–242°.

EXAMPLE 82

1-(4-Chloro-benzyl)-piperidin-4-yl 4-chloro-benzoate a) 0.226 g (0.001 mol) of 1-(4-chloro-benzyl)-piperidin-4-ol and 0.350 ml (0.0025 mol) of triethylamine were dissolved in 10 ml of toluene, treated with 0.16 ml (0.00125 mol) of 4-chloro-benzoyl chloride and boiled at reflux for 18 hrs. The reaction mixture was concentrated and the residue was chromatographed over silica gel with ethyl acetate/hexane (1:3). 0.28 g (77%) of 1-(4-chloro-benzyl)-piperidin-4-yl 4-chloro-benzoate was obtained as colorless crystals; m.p. 67°–69°.

b) 0.182 g (0.0005 mol) of 1-(4-chloro-benzyl)-piperidin-4-yl 4-chloro-benzoate was dissolved in 15 ml of ether, filtered, diluted with 0.5 ml of methanol and treated with 5 ml of 1N ethereal HCl. The separated precipitate was filtered off and dried. 0.17 g (85%) of 1-(4-chloro-benzyl)-piperidin-4-yl 4-chloro-benzoate hydrochloride (1:1) was obtained as white crystals; m.p. 235°–237°.

EXAMPLE 83

1-(4-Chloro-benzyl)-piperidin-4-yl 4-fluoro-benzoate a) 0.226 g (0.001 mol) of 1-(4-chloro-benzyl)-piperidin-4-ol was dissolved in 5 ml of dimethylformamide and treated with 0.061 g (0.0005 mol) of dimethylaminopyridine and 0.14 g (0.001 mol) of 4-fluoro-benzoic acid. The mixture was cooled to 0° and 0.211 g (0.0011 mol) of N-ethyl-N'-(3-dimethylamino-propyl)-carbodiimide hydrochloride was added. The mixture was warmed to room temperature and stirred for 72 hrs. The solvent was distilled off and the residue was taken up in ethyl acetate and treated with silica gel. After removal of the solvent the residue was chromatographed on silica gel with ethyl acetate/hexane (1:2) as the eluent. 0.29 g (83%) of 1-(4-chloro-benzyl)-piperidin-4-yl 4-fluoro-benzoate was obtained as a colorless oil.

b) 0.285 g (0.00082 mol) of 1-(4-chloro-benzyl)-piperidin-4-yl 4-fluoro-benzoate was dissolved in 25 ml of ether, filtered, diluted with 8.5 ml of methanol and treated with 8.2 ml of 1N ethereal HCl. The separated precipitate was filtered off and dried. 0.277 g (88%) of 1-(4-chloro-benzyl)-piperidin-4-yl 4-fluoro-benzoate hydrochloride (1:1) was obtained as white crystals; m.p. 214°.

EXAMPLE 84

1-(4-Bromo-benzyl)-piperidin-4-yl 4-fluoro-benzoate a) 0.428 g (0.00184 mol) of 1-(4-bromo-benzyl)-piperidin-4-ol was dissolved in 8 ml of dimethylformamide and treated with 0.097 g (0.00079 mol) of dimethylaminopyridine and 0.222 g (0.00158 mol) of 4-fluoro-benzoic acid. The mixture was cooled to 0° and 0.334 g (0.00174 mol) of N-ethyl-N'-(3-dimethylaminopropyl)-carbodiimide hydrochloride was added. The mixture was warmed to room temperature and stirred for 18 hrs. The solvent was distilled off and the residue was taken up in ethyl acetate and treated with silica gel. After removal of the solvent the residue was chromatographed on silica gel with ethyl acetate/hexane (1:2) as the eluent. 0.47 g (76%) of 1-(4-bromo-benzyl)-piperidin-4-yl 4-fluoro-benzoate was obtained as a colorless oil.

b) 0.196 g (0.0005 mol) of 1-(4-bromo-benzyl)-piperidin-4-yl 4-fluoro-benzoate was dissolved in 15 ml of ether, filtered, diluted with 0.5 ml of methanol and treated with 5 ml of 1N ethereal HCl. The separated precipitate was filtered off and dried. 0.198 g (98%) of 1-(4-bromo-benzyl)-piperidin-4-yl 4-fluoro-benzoate hydrochloride (1:1) was obtained as white crystals; m.p. 224°–226°.

EXAMPLE 85

Phenyl 1-benzylpiperidin-4-carboxylate a) 4.62 ml (0.03 mol) of ethyl piperidine-4-carboxylate were dissolved in 50 ml of dimethylformamide and treated with 4.98 ml (0.036 mol) of triethylamine. 3.9 ml (0.033 mol) of benzyl bromide were added while cooling with ice and the mixture was stirred for 10 min., warmed to 40° and stirred under an argon atmosphere for 18 hrs. The solvent was then distilled off, the residue was added to 100 ml of water, extracted three times with 100 ml of ether each time and the organic phase was dried over magnesium sulfate. 5.33 g (72%) of ethyl 1-benzyl-piperidine-4-carboxylate were obtained as a yellow oil. MS: me/e=248 ($C_{15}H_{22}NO_2^+$).

b) 0.8 g (0.00323 mol) of ethyl 1-benzylpiperidine-4-carboxylate was dissolved in a mixture of 5 ml of dioxan, 2 ml of water and 3.5 ml (0.0035 mol) of 1N aqueous NaOH. After stirring for 15 min. 3.5 ml (0.0035 mol) of 1N aqueous HCl were added, the mixture was diluted with 20 ml of water, the dioxan was removed by distillation and the residue which remained was lyophilized. The residue was boiled twice with 100 ml of isopropanol each time and the combined organic phases were filtered and concentrated. The product crystallized out in the cold. 0.586 g (83%) of 1-benzylpiperidine-4-carboxylic acid was obtained as white crystals; m.p. 167°–168°.

c) 0.33 g (0.0015 mol) of 1-benzylpiperidine-4-carboxylic acid was dissolved in 5 ml of oxalyl chloride for 2 hrs. The excess oxalyl chloride was distilled off. The residue was taken up twice in toluene and concentrated each time. 0.355 g (99%) of 1-benzyl-piperidine-4-carboxylic acid chloride was obtained as a pale beige solid. This was dissolved in 20 ml of toluene, treated with 0.3 ml (0.00224 mol) of triethylamine and 0.184 g (0.00195 mol) of phenol and boiled at reflux for 18 hrs. After removal of the solvent the residue was chromatographed on silica gel with ether/hexane (1:2.5→1:2) as the eluent. 0.315 g (71%) of phenyl 1-benzyl-piperidin-4-carboxylate was obtained as a yellow oil. MS: me/e=296 ($C_9H_{22}NO_2^+$).

d) 0.3 g (0.00101 mol) of phenyl 1-benzylpiperidine-4-carboxylate was dissolved in 15 ml of ether, filtered, diluted with 1.5 ml of methanol and treated with 2 ml of 1N ethereal HCl. The mixture was stirred for 2 hrs. The separated precipitate was filtered off, washed with ether and dried in a high vacuum. 0.288 g (87%) of phenyl 1-benzylpiperidine-4-carboxylate hydrochloride (1:1) was obtained as white crystals; m.p. 182°–183°.

EXAMPLE 86

Benzyl 1-benzylpiperidin-4-carboxylate a) 0.278 g (0.00127 mol) of 1-benzylpiperidine-4-carboxylic acid was boiled at reflux in 5 ml of oxalyl chloride for 2 hrs. The excess oxalyl chloride was distilled off. The residue was taken up twice in toluene and concentrated each time. 0.3 g (99%) of 1-benzylpiperidine-4-carboxylic acid chloride was obtained as a pale beige solid. This was dissolved in 20 ml of toluene, treated with 0.265 ml (0.0019 mol) of triethylamine and 0.17 g (0.00165 mol) of benzyl alcohol and boiled at reflux for 18 hrs. After removal of the solvent the residue was chromatographed on silica gel with ether/hexane (1:2) as the eluent. 0.246 g (80%) of benzyl 1-benzylpiperidin-4-carboxylate was obtained as a yellow oil. MS: me/e=310 ($C_2H_{23}NO_2^+$).

b) 0.23 g (0.00074 mol) of benzyl 1-benzylpiperidine-4-carboxylate was dissolved in 13 ml of ether, filtered, diluted with 1.3 ml of methanol and treated with 1.5 ml of 1N ethereal HCl. The mixture was stirred for 2 hrs. The separated precipitate was filtered off, washed with ether and dried in a high vacuum. 0.226 g (88%) of benzyl 1-benzyl-piperidine-4-carboxylate hydrochloride (1:1) was obtained as white crystals; m.p. 148°–149°.

EXAMPLE 87

1-Benzylpiperidin-4-ylmethyl benzoate a) 1.42 g (0.0375 mol) of lithium aluminium hydride were suspended in 20 ml of THF. 1.548 g (0.00623 mol) of ethyl 1-benzylpiperidine-4-carboxylate were slowly added dropwise at 0°. The mixture was heated to 70° and boiled at reflux for 16 hrs. The reaction mixture was treated with 70 ml of ethyl acetate, 6.5 ml of water and 1.5 ml of 2N aqueous NaOH. The mixture was stirred for 1 hr., the precipitate was filtered off and the filtrate was concentrated. The residue was chromatographed on silica gel with methanol/dichloromethane (1:9) as the eluent. 1.16 g (91%) of 1-benzyl-4-hydroxymethylpiperidine were obtained.

b) 0.248 g (0.00121 mol) of 1-benzyl-4-hydroxymethyl-piperidine was dissolved in 5 ml of toluene and treated with 0.2 ml (0.00145 mol) of triethylamine and 0.155 ml (0.00133 mol) of benzoyl chloride. The mixture was boiled at reflux for 18 hrs., the solvent was distilled off and the residue was taken up in ether. The organic phase was washed with water and saturated sodium chloride solution and dried over magnesium sulfate. It was concentrated and the residue was chromato-graphed on silica gel with ethyl acetate/hexane (1:1) as the eluent. 0.2 g (53%) of 1-benzylpiperidin-4-ylmethyl benzoate was obtained as a yellow oil. MS: me/e (% basic peak)=309 ($C_{20}H_{23}NO_2^+$, 18), 308 (17), 232 (14), 204 (41), 159 (18.6), 105 (25.5), 91 (100).

c) 0.2 g (0.00065 mol) of 1-benzylpiperidin-4-ylmethyl benzoate was dissolved in 10 ml of ether, filtered, diluted with 1 ml of methanol and treated with 1 ml of 1N ethereal HCl. The mixture was stirred for 2 hrs. The separated precipitate was filtered off, washed with ether and dried in a high vacuum. 0.18 g (80%) of 1-benzyl-piperidin-4-ylmethyl benzoate hydrochloride (1:1) was obtained as white crystals; m.p. 201°–202°.

EXAMPLE 88

1-Benzyl-4-phenoxymethylpiperidine a) 0.3 g (0.00146 mol) 1-benzyl-4-hydroxymethyl-piperidine, 0.137 g (0.00146 mol) of phenol and 0.45 g (0.0017 mol) of triphenylphosphine were dissolved in 10 ml of toluene, cooled to 10° and treated slowly with 0.264 ml (0.0017 mol) of diethyl azodicarboxylate. The mixture was stirred at 90° for 25 hrs. The solvent was removed, the residue was taken up in ethyl acetate, washed three times with 40 ml of water each time and three times with 40 ml of 2N aqueous NaOH each time and the organic phase was dried over magnesium sulfate. The solvent was removed. The residue was chromatographed on silica gel with ethyl acetate/hexane (1:2) as the eluent. 0.17 g (41.4%) 1-benzyl-4-phenoxymethylpiperidine was obtained as white crystals; m.p. 56°–57°.

b) 0.165 g (0.00059 mol) 1-benzyl-4-phenoxymethyl-piperidine was dissolved in 5 ml of ether, filtered, diluted with 0.5 ml of methanol and treated with 1 ml of 1N ethereal HCl. The mixture was stirred for 2 hrs. The separated precipitate was filtered off, washed with ether and dried in a high vacuum. 0.165 g (88.5%) of 1-benzyl-4-phenoxymethylpiperidine hydro-chloride (1:1) was obtained as white crystals; m.p. 203°–204°.

EXAMPLE 89

1-Benzyl-4-benzyloxypiperidine a) 0.574 g (0.003 mol) of 1-benzyl-4-hydroxypiperidine dissolved in 5 ml of dimethylformamide was added dropwise at 0° to a suspension of 0.14 g (0.0035 mol) of sodium hydride in 5 ml of dimethylformamide. The mixture was left to warm to room temperature and was stirred for 1.5 hrs. Then, 0.39 ml (0.0033 mol) of benzyl bromide was added dropwise. The mixture was stirred at 40° for 18 hrs. The solvent was removed, the residue was taken up in water, adjusted to pH 11 with 2N aqueous NaOH and extracted with ether. The organic phase was dried over magnesium sulfate and concentrated. The residue was chromatographed on silica gel with ethyl acetate/hexane (1:1) as the eluent. 0.333 g (40%) of 1-benzyl-4-benzyloxypiperidine was obtained as a yellow oil. MS: me/e=282 ($C_9H_{24}NO^+$).

b) 0.19 g (0.00067 mol) of 1-benzyl-4-benzyloxy-piperidine was dissolved in 5 ml of ether, filtered, diluted with 0.5 ml of methanol and treated with 1 ml of 1N ethereal HCl. The mixture was stirred for 2 hrs. The separated precipitate was filtered off, washed with ether and dried in a high vacuum. 0.166 g (78%) of 1-benzyl-4-benzyloxypiperidine hydrochloride (1:1) was obtained as white crystals; m.p. 165°–167°.

EXAMPLE 90

1-Benzyl-4-phenylsulfanylmethylpiperidine a) 18 ml (0.117 mol) of ethyl piperidine-4-carboxylate and 32.4 ml (0.2325 mol) of triethylamine were dissolved in 580 ml of toluene and treated with 18 ml (0.155 mol) of benzoyl chloride. The mixture was stirred at room temperature for 2 hrs., filtered and the solvent was evaporated. The residue was chromatographed on silica gel with ethyl acetate/hexane (1:3→1:1) as the eluent. 28.3 g (92%) of ethyl 1-benzoyl-4-piperidine-carboxylate were obtained as white crystal; m.p. 75°–78°.

b) 10.4 g (0.04 mol) of ethyl 1-benzoyl-4-piperidine-carboxylate were dissolved in 90 ml of THF and treated with a solution of 0.871 g (0.04 mol) of lithium borate in 20 ml of THF. 0.45 ml (0.004 mol) of trimethyl borate was added and the mixture was stirred at room temperature for 60 hrs. The reaction mixture was treated with water and stirred for 1.5 hrs. The mixture was extracted with ethyl acetate and the organic phase was washed with water and saturated sodium chloride solution and dried over sodium sulfate. The residue was chromatographed on silica gel with ethyl acetate/hexane (1:1). 7.8 g (90%) of 1-benzoyl-4-hydroxymethyl-piperidine were obtained as white crystals; m.p. 84°–87°.

c) 7.5 g (0.0342 mol) of 1-benzoyl-4-hydroxymethyl-piperidine were dissolved in 170 ml of dichlormethane and 17 ml (0.122 mol) of triethylamine, cooled to 0° and treated with a solution of 3.14 ml (0.0404 mol) of methanesulfonyl chloride in 20 ml of dichloromethane. The mixture was stirred at 0° for ½ hr. Then, 100 ml of 1N aqueous HCl were added, the mixture was stirred for 5 min., the organic phase was washed with 1N aqueous HCl, with saturated bicarbonate solution and with saturated sodium chloride solution and dried over sodium sulfate. 10.2 g (100%) of 1-benzoylpiperidin-4-ylmethyl methanesulfonate were obtained as yellow crystals; m.p. 87°–90°.

d) 4.27 g (0.1068 mol) of sodium hydride (60% dispersion in oil) were washed twice with hexane, suspended in 160 ml of THF and treated with 10.3 ml (0.1068 mol) of thiophenol. The mixture was stirred for 15 min. and then a solution of 5.95 g (0.02 mol) of 1-benzoylpiperidin-4-yl-methyl methanesulfonate in 20 ml of THF was added. The mixture was boiled at reflux for 18 hrs. The reaction mixture was treated with 250 ml of 2N aqueous NaOH and extracted with ether. The organic phase was washed with 2N aqueous NaOH and saturated sodium chloride solution, dried over sodium sulfate and concentrated. The residue was chromatographed on silica gel with ethyl acetate/hexane (1:3) as the eluent. 5.8 g (93%) of 1-benzoyl-4thio-phenoxymethylpiperidine were obtained as yellow crystals; m.p. 76°–79°.

e) 40 ml (0.04 mol) of 1M $BH_3$ in THF were added to a solution of 3.11 g (0.01 mol) of 1-benzoyl-4-thiophenoxymethyl-piperidine in 50 ml of THF. The mixture was boiled at reflux for 16 hrs. Then, 90 ml of 1N aqueous HCl were added and the mixture was stirred for 1.5 hrs. It was extracted with ether and concentrated and the residue was taken up in a mixture of 20 ml of glacial acetic acid and 20 ml of THF and boiled at reflux for 3 hrs. The solvents were distilled off and the residue was taken up in ethyl acetate, washed with saturated sodium carbonate solution and sodium chloride solution and dried over sodium sulfate. The solvent was removed and the residue was chromatographed on silica gel with ethyl acetate/hexane (1:9) as the eluent. 2.3 g (77%) of 1-benzyl-4-phenylsulfanylmethyl-piperidine were obtained as a colorless oil. MS: me/e=298 ($C_{19}H_{24}NS^+$).

f) 0.18 g (0.0005 mol) of 1-benzyl-4-phenylsulfanyl-methylpiperidine was dissolved in 15 ml of ether, filtered, diluted with 1 ml of methanol and treated with 5 ml of 1N ethereal HCl. The mixture was stirred for 2 hrs. The separated precipitate was filtered off, washed with ether and dried in a high vacuum. 0.135 g (81%) of 1-benzyl-4-phenylsulfanylmethyl-piperidine hydrochloride (1:1) was obtained as white crystals; m.p. 169°–172°.

EXAMPLE 91

(RS)-4-Benzosulfinylmethyl-1-benzylpiperidine a) 0.297 g (0.001 mol) of 1-benzyl-4-phenylsulfanyl-methylpiperidine was dissolved in 40 ml of a mixture of methanol/water (1:1). 1.07 g (0.005 mol) of sodium periodate were added and the mixture was stirred at room temperature for ½ hr. Then, the pH was adjusted to >11 with 1N aqueous NaOH and the reaction mixture was extracted with ethyl acetate. The organic phase was washed with saturated sodium chloride solution, dried over sodium sulfate and concentrated. The residue was chromatographed on silica gel with ethyl acetate/hexane (1:1→1:0) as the eluent. 0.26 g (83%) of (RS)-4-benzo-sulfinylmethyl-1-benzylpiperidine was obtained as white crystals; m.p. 98°–100°.

b) 0.222 g (0.00071 mol) of (RS)-4-benzosulfinylmethyl-1-benzylpiperidine was dissolved in 10 ml of ether, filtered, diluted with 1 ml of methanol and treated with 5 ml of 1N ethereal HCl. The mixture was stirred for 2 hrs. The mixture was decanted and the residue was treated with ether/ethanol, with a viscous precipitate being obtained. This was filtered off, washed with ether and dried in a high vacuum. 0.19 g (77%) of (RS)-4-phenylsulfinyl-methyl-1-benzylpiperidine hydrochloride (1:1) was obtained as white crystals; m.p. 200°–203°.

EXAMPLE 92

4-Benzosulfonylmethyl-1-benzylpiperidine a) 0.297 g (0.001 mol) of 1-benzyl-4-phenylsulfanyl-methylpiperidine was dissolved in 40 ml of a mixture of methanol/water (1:1). 4.3 g (0.02 mol) of sodium periodate were added and the mixture was stirred at room temperature for 72 hrs. Then, the pH was adjusted to >11 with 1N aqueous NaOH and the reaction mixture was extracted with ethyl acetate. The organic phase was washed with saturated sodium chloride solution, dried over sodium sulfate and concentrated. The residue was chromatographed on silica gel with ethyl acetate/hexane (1:1) as the eluent. 0.255 g (77%) of 4-benzosulfonylmethyl-1-benzylpiperidine was obtained as white crystals; m.p. 105°–107°.

b) 0.23 g (0.0007 mol) of 4-benzosulfonylmethyl-1-benzylpiperidine was dissolved in 10 ml of ether, filtered, diluted with 1 ml of methanol and treated with 5 ml of 1N ethereal HCl. The mixture was stirred for 2 hrs. The precipitate was filtered off, washed with ether and dried in a high vacuum. 0.22 g (86%) 4-benzosulfonylmethyl-1-benzylpiperidine hydrochloride (1:1) was obtained as white crystals; m.p. 152°–155°.

EXAMPLE 93

1-Benzyl-4-benzylsulfanyl-piperidine a) 2.0 g (0.01045 mol) of 1-benzyl-4-hydroxypiperidine were dissolved in 20 ml of dichlormethane and 5.1 ml (0.0366 mol) of triethylamine, cooled to 00 and treated with a solution of 1 ml (0.01255 mol) of methanesulfonyl chloride in 5 ml of dichloromethane. The mixture was stirred at 0° for ½ hr. Then, 10ml of 1N aqueous HCl were added, the mixture was stirred for 5 min. and the organic phase was washed with 1N aqueous HCl, with saturated bicarbonate solution and saturated sodium chloride solution and dried over magnesium sulfate. 0.97 g (35%) of 1-benzylpiperidin-4-yl methanesulfonate was obtained as yellow crystals. MS: me/e=270 ($C_{13}H_{20}NO_3S^+$).

b) 0.8 g (0.02 mol) of sodium hydride (60% dispersion in oil) was washed three times with hexane and suspended in 20 ml of THF. 2.24 ml (0.019 mol) of benzyl mercaptan in 12 ml of THF were added dropwise at 0°. The mixture was stirred at room temperature for 15 min. and subsequently 0.95 g (0.0037 mol) of 1-benzylpiperidin-4-yl methanesulfonate in 10 ml of THF was added dropwise. The reaction mixture was boiled at reflux for 22 hrs. and then poured into 200 ml of 2N aqueous NaOH. The inorganic phase was extracted with ether and the combined organic phases were washed with 2N aqueous NaOH and dried over magnesium sulfate. The residue was chromatographed on silica gel with ethyl acetate/hexane (1:3→1:1) as the eluent. 0.444 g (40%) of 1-benzyl-4-benzylsulfanylpiperidine was obtained as a yellow oil. MS: me/e (% basic peak)=297 ($C_{19}H_{23}NS^+$, 1.4), 206 (62), 174 (23), 91 (199).

c) 0.08 g (0.00027 mol) of 1-benzyl-4-benzylsulfanyl-piperidine was dissolved in 8 ml of ether, filtered, diluted with 0.8 ml of methanol and treated with 2 ml of 1N ethereal HCl. The mixture was stirred for 2 hrs. The precipitate was filtered off, washed with ether and dried in a high vacuum. 0.06 g (66%) of 1-benzyl-4-benzylsulfanylpiperidine hydrochloride (1:1) was obtained as white crystals; m.p. 167°–168°.

EXAMPLE 94

(RS)-1-benzyl-4-benzylsulfinylpiperidine a) 0.37 g (0.00124 mol) of 1-benzyl-4-benzylsulfanyl-piperidine was suspended in a mixture of 20 ml of water/methanol (1:1) and treated with 2.66 g (0.0124 mol) of sodium periodate. The mixture was stirred at room temperature for 3 hrs., 150 ml of water were added, the pH was adjusted to 8–9 with 1N aqueous NaOH, the mixture was extracted with ethyl acetate and the organic phase was dried over magnesium sulfate. The solvent was removed on a rotary evaporator and the residue was chromatographed on silica gel with methanol/dichloro-methane (1:19). The fraction having $R_f$ 0.31 was the desired product. 0.17 g (44%) of (RS)-1-benzyl-4-benzylsulfinyl-piperidine was obtained as white crystals; m.p. 123°–125'0.

b) 0.06 g (0.00019 mol) of (RS)-1-benzyl-4-benzylsulfinylpiperidine was dissolved in 6 ml of ether, filtered, diluted with 0.6 ml of methanol and treated with 0.5 ml of 1N ethereal HCl. The mixture was stirred for 2 hrs. and the precipitate was filtered off, washed with ether and dried in a high vacuum. 0.056 g (84%) of (RS)-1-benzyl-4-benzylsulfinylpiperidine hydrochloride (1:1) was obtained as white crystals; m.p. 212°–213°.

EXAMPLE 95

1-Benzyl-4-benzylsulfonylpiperidine a) The fraction having $R_f$ 0.4 from the chromatography. described under Example 94 a) was the desired sulfone. 0.063 g (15%) of 1-benzyl-4-benzylsulfonylpiperidine was obtained as white crystals; m.p. 120°–121°.

b) 0.052 g (0.000158 mol) of 1-benzyl-4-benzylsulfonylpiperidine was dissolved in 10 ml of ether, filtered, diluted with 1 ml of methanol and treated with 0.5 ml of 1N ethereal HCl. The mixture was stirred for 2 hrs. The precipitate was filtered off, washed with ether and dried in a high vacuum. 0.045 g (78%) of 1-benzyl-4-benzylsulfonylpiperidine hydro-chloride (1:1) was obtained as white crystals; m.p. 261°–264°.

EXAMPLE A

Tablets of the following composition are produced in the usual manner:

|  | mg/tablet |
| --- | --- |
| Active ingredient | 100 |
| Powd. lactose | 95 |
| White corn starch | 35 |
| Polyvinylpyrrolidone | 8 |
| Na carboxymethyl starch | 10 |
| Magnesium stearate | .2 |
| Tablet weight | 250 |

EXAMPLE B

Tablets of the following composition are produced in the usual manner:

|  | mg/tablet |
| --- | --- |
| Active ingredient | 100 |
| Powd. lactose | 100 |
| White corn starch | 64 |
| Polyvinylpyrrolidone | 12 |
| Na carboxymethyl starch | 20 |
| Magnesium stearate | 4 |
| Tablet weight | 400 | wherein

A is

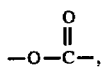

B is

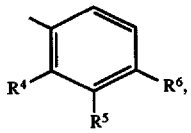

at least one of $R^1$, $R^2$ and $R^3$ are lower alkyl and the remainder of $R^1$, $R^2$ and $R^3$ are hydrogen; and $R^4$, $R^5$ and $R^6$ are independently hydrogen, nitro, halogen, lower-alkyl, lower-alkoxy, cyano, trifluoromethyl, amino, lower-alkylamino or di-lower-alkylamino;

and pharmaceutically acceptable salts thereof.

6. Compounds of the formula

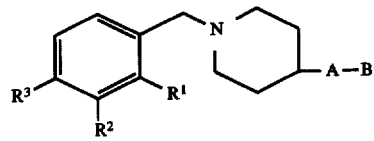

wherein

A is

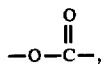

B is

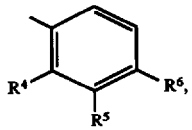

at least one of $R^1$, $R^2$ and $R^3$ are halogen and the remainder of $R^1$, $R^2$ and $R^3$ is hydrogen; and $R^4$, $R^5$ and $R^6$ are independently hydrogen, nitro, halogen, lower-alkyl, lower-alkoxy, cyano, trifluoromethyl, amino, lower-alkylamino or di-lower-alkylamino;

and pharmaceutically acceptable salts thereof.

7. Compounds of the formula

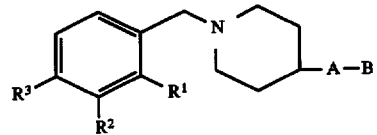

wherein

A is

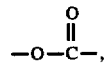

B is

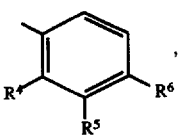

at least one of $R^1$, $R^2$ and $R^3$ are nitro and the remainder of $R^1$, $R^2$ and $R^3$ is hydrogen; and $R^4$, $R^5$ and $R^6$ are independently hydrogen, nitro, halogen, lower-alkyl, lower-alkoxy, cyano, trifluoromethyl, amino, lower-alkylamino or di-lower-alkylamino; and and pharmaceutically acceptable salts thereof.

8. Compounds of the formula

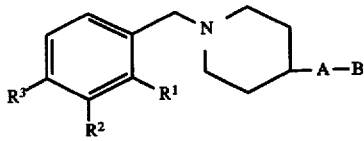

wherein

A is

B is

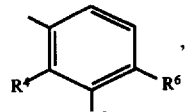

at least one of $R^1$, $R^2$ and $R^3$ is amino and the remainder of $R^1$, $R^2$ and $R^3$ are hydrogen; and $R^4$, $R^5$ and $R^6$ are independently hydrogen, nitro, halogen, lower-alkyl, lower-alkoxy, cyano, trifluoromethyl, amino, lower-alkylamino or di-lower-alkylamino;

and pharmaceutically acceptable salts thereof.

9. Compounds of the formula

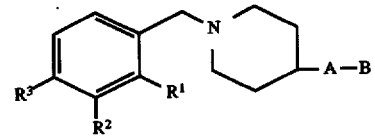

wherein

A is

B is

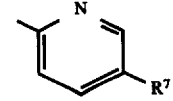

$R^1$, $R^2$ and $R^3$ are independently hydrogen, amino, nitro, halogen, lower-alkyl or lower-alkoxy; and $R^7$, is hydrogen amino or nitro;

and pharmaceutically accepatable salts thereof.

10. Compounds of the formula

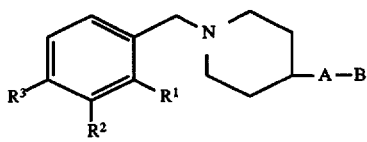

wherein
A is

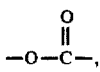

B is

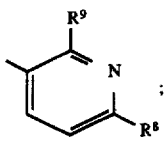

$R^1$, $R^2$ and $R^3$ are independently hydrogen, amino, nitro halogen, lower-alkyl or lower-alkoxy;

$R^4$, $R^5$ and $R^6$ are independently hydrogen, nitro, halogen lower-alkyl, lower-alkoxy, cyano, trifluoromethyl, amino, lower-alkylamino or di-lower-alkylamino; and $R^8$ and $R^9$ are independently hydrogen, amino or nitro, and pharmaceutically acceptable salts thereof.

11. Compounds of the formula

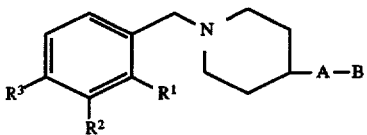

wherein
A is

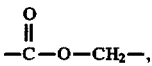

B is

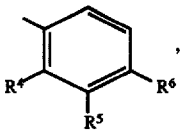

$R^1$, $R^2$ and $R^3$ are independently hydrogen, amino, nitro, halogen, lower-alkyl or lower-alkoxy; and $R^4$, $R^5$ and $R^6$ are independently hydrogen, nitro, halogen, lower-alkyl, lower-alkoxy, cyano, trifluoromethyl, amino, lower-alkylamino or di-lower-alkylamino;

and pharmaceutically acceptable salts thereof.

12. A compound selected from the group consisting of:
1-benzyl-piperidin-4-yl 2-amino-benzoate;
1-benzyl-piperidin-4-yl 2,4-diamino-benzoate;
1-benzyl-piperidin-4-yl 3-amino-benzoate;
1-benzyl-piperidin-4-yl 3-dimethylamino-benzoate;
1-benzyl-piperidin-4-yl 2-dimethylamino-benzoate; and
1-benzyl-piperidin-4-yl 4-dimethylamino-benzoate,
and pharmaceutically acceptable salts thereof.

13. The compound of claim 12 wherein said compound is 1-benzyl-piperidin-4-yl 2-amino-benzoate.

14. The compound of claim 12 wherein said compound is 1-benzyl-piperidin-4-yl 2,4-diamino-benzoate.

15. The compound of claim 12 wherein said compound is 1-benzyl-piperidin-4-yl 3-amino-benzoate.

16. The compound of claim 12 wherein said compound is 1-benzyl-piperidin-4-yl 3-dimethylamino-benzoate.

17. The compound of claim 12 wherein said compound is 1-benzyl-piperidin-4-yl 2-dimethylamino-benzoate.

18. The compound of claim 12 wherein said compound is 1-benzyl-piperidin-yl 4-dimethylamino-benzoate.

19. The compound of claim 12 wherein said compound is 1-benzyl-piperidin-4-yl 3-dimethylamino-benzoate.

20. The compound 1-benzyl-piperidin-4-yl 2-amino-4-fluoro-benzoate.

21. The compound 1- benzyl-4-yl 2-amino-4-chloro-benzoate.

22. The compound 1-benzyl-piperidin-4-yl 4-iodo-2-amino-benzoate.

23. The compound 1-benzyl-piperidin-4-yl 2-amino-4-trifluoromethyl-benzoate.

24. The compound of claim 1 wherein said compound is 1-benzyl-piperidin-4-yl 4-bromo-benzoate.

25. The compound of claim 1 wherein said compound is 1-benzyl-piperidin-4-yl 4-iodo-benzoate.

26. The compound of claim 1 wherein said compound is 1-benzyl-piperidin-4-yl 2-fluoro-benzoate.

27. The compound of claim 1 wherein said compound is 1-benzyl-piperidin-4-yl 3-fluoro-benzoate.

28. The compound of claim 1 wherein said compound is 1-benzyl-piperidin-4-yl 2-chloro-benzoate.

29. The compound of claim 1 wherein said compound is 1-benzyl-piperidin-4-yl 2-bromo-benzoate.

30. The compound of claim 1 wherein said compound is 1-benzyl-piperidin-4-yl 3-bromo-benzoate.

31. The compound of claim 1 wherein said compound is 1-benzyl-piperidin-4-yl 2-iodo-benzoate.

32. The compound of claim 1 wherein said compound is 1-benzyl-piperidin-4-yl 3-iodo-benzoate.

33. The compound of claim 2 wherein said compound is 1-benzyl-piperidin-4-yl 4-methyl-benzoate.

34. The compound of claim 2 wherein said compound is 1-benzyl-piperidin-4-yl 2-methyl-benzoate.

35. The compound of claim 2 wherein said compound is 1-benzyl-piperidin-4-yl 3-methyl-benzoate.

36. The compound of claim 2 wherein said compound is 1-benzyl-piperidin-4-yl 2,4-dimethyl-benzoate.

37. The compound of claim 3 wherein said compound is 1-benzyl-piperidin-4-yl 2-amino-4-methyl-benzoate.

38. The compound 1-benzyl-piperidin-4-yl 4-bromo-2-methyl-benzoate.

39. The compound 1-benzyl-piperidin-4-yl 2-amino-4-methyl-benzoate.

40. The compound 1-benzyl-piperidin-4-yl 2-nitro-4-trifluoromethyl-benzoate.

41. The compound 1-benzyl-piperidin-4-yl 4-bromo-2-nitro-benzoate.

42. The compound 1-benzyl-piperidin-4-yl 4-iodo-2-nitro-benzoate.

43. The compound of claim 4 wherein said compound is 1-benzyl-piperidin-4-yl 2-methoxy-benzoate.

44. The compound of claim 4 wherein said compound is 1-benzyl-piperidin-4-yl 3-methoxy-benzoate.

45. The compound of claim 4 wherein said compound is 1-benzyl-piperidin-4-yl 4-methoxy-benzoate.

46. The compound of claim 5 wherein said compound is 1-(4-methyl-benzyl)-piperidin-4-yl benzoate.

47. The compound of claim 5 wherein said compound is 1-(4-methyl-benzyl)-piperidin-4-yl 4-methyl-benzoate.

48. The compound of claim 6 wherein said compound is 1-(4-chloro-benzyl)-piperidin-4-yl benozoate.

49. The compound of claim 6 wherein said compound is 1-(4-chloro-benzyl)-piperidin-4-yl 4-methyl-benzoate.

50. The compound of claim 6 wherein said compound is 1-(4-chloro-benzyl)-piperidin-4-yl 4-chloro-benzoate.

51. The compound of claim 6 wherein said compound is 1-(4-bromo-benzyl)-piperidin-4-yl benozoate.

52. The compound of claim 6 wherein said compound is 1-(4-fluoro-benzyl)-piperidin-4-yl benozoate.

53. The compound of claim 7 wherein said compound is 1-(3-nitro-benzyl)-piperidin-4-yl benozoate.

54. The compound of claim 7 wherein said compound is 1-(3-nitro-benzyl)-piperidin-4-yl 4-methyl-benzoate.

55. The compound of claim 8 wherein said compound is 1-(3-amino-benzyl)-piperidin-4-yl 4-methyl-benzoate.

56. The compound of claim 8 wherein said compound is 1-(2-amino-benzyl)-piperidin-4-yl 4-methyl-benzoate.

57. The compound of claim 8 wherein said compound is 1-(3-amino-benzyl)-piperidin-4-yl benzoate.

58. The compound of claim 8 wherein said compound is 1-(4-amino-benzyl)-piperidin-4-yl benzoate.

59. A compound wherein said compound is 1-(4-methoxy-benzyl)-piperidin-4-yl benzoate.

60. The compound of claim 9 wherein said compound is 1-benzyl-piperidin-4-yl 5-amino-picolinate.

61. The compound of claim 9 wherein said compound is 1-benzyl-piperidin-4-yl 5-nitro-picolinate.

62. The compound of claim 10 wherein said compound is 1-benzyl-piperidin-4-yl 6-amino-nicotinate.

63. The compound of claim 10 wherein said compound is 1-benzyl-piperidin-4-yl 2-amino-nicotinate.

64. The compound of claim 11 wherein said compound is benzyl 1-benzylpiperidin-4-carboxylate.

65. The compound 1-benzylpiperidin-4-yl methyl benzoate.

* * * * *